(12) United States Patent
Elbaum et al.

(10) Patent No.: US 6,201,880 B1
(45) Date of Patent: *Mar. 13, 2001

(54) METHOD AND APPARATUS FOR ELECTRONICALLY IMAGING A TOOTH THROUGH TRANSILLUMINATION BY LIGHT

(75) Inventors: Marek Elbaum, Dobbs Ferry; Michael Greenebaum, Brooklyn, both of NY (US); Adam Jacobs, Glen Ridge, NJ (US); Sunguk Keem, Cliffside Park, NJ (US); Allen H. Schneiderman, Ridgewood, NJ (US); Theodore S. Shultz, Larchmont, NY (US)

(73) Assignee: Electro-Optical Sciences, Irvington, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/778,001

(22) Filed: Dec. 31, 1996

(51) Int. Cl.$^7$ ..................................................... G06K 9/00
(52) U.S. Cl. ......................... 382/100; 382/115; 382/128; 433/29; 348/66
(58) Field of Search .................................. 382/100, 115, 382/128, 212, 218; 433/29, 30, 43, 44; 348/66, 68

(56) References Cited

U.S. PATENT DOCUMENTS

| | | | |
|---|---|---|---|
| 2,840,070 | 6/1958 | Tofflemire | 128/11 |
| 3,152,587 | 10/1964 | Ullrich et al. | 128/2 |
| 4,074,306 | 2/1978 | Kakinuma et al. | 358/1 |
| 4,077,399 | 3/1978 | Le Roy | 128/23 |
| 4,162,618 | 7/1979 | Okuda | 64/23 |
| 2591094 | 6/1987 | (FR) | A61B/1/24 |
| 4,168,882 | 9/1979 | Hopkins | 350/54 |

(List continued on next page.)

FOREIGN PATENT DOCUMENTS

| | | | |
|---|---|---|---|
| 2 208 902 | 8/1973 | (DE) | A61C/19/04 |
| 2308 554 | 8/1974 | (DE) | A61N/5/06 |
| 2505798 A1 | 8/1976 | (DE) | A61B/1/04 |
| 3045162 A1 | 7/1982 | (DE) | A61B/1/24 |
| 3233410 A1 | 4/1984 | (DE) | F21S/1/00 |
| 4307411 A1 | 9/1994 | (DE) | A61B/6/00 |
| 0 122 537 A1 | 10/1984 | (EP) | G02B/23/08 |
| 0 184 778 A2 | 6/1986 | (EP) | A61B/1/00 |
| 0 282 832 A1 | 9/1988 | (EP) | A61B/1/24 |
| 0 296 520 A2 | 12/1988 | (EP) | A61C/19/04 |

(List continued on next page.)

OTHER PUBLICATIONS

Vaarkamp, S., "Propagation of Light Through Human Pental Enamel and Dentine," Journal of ORCA, 1995, pp. 8–13.*
Verdonschot, E.H., "Optical Quantitation and Radiographic Diagnosis of Incipient Approximal Caries Lesions", 1991, pp. 359–364.*
Mallat, S., "Wavelet Maxima Representation", 1989, pp. 208–214.*

(List continued on next page.)

Primary Examiner—Matthew C. Bella
(74) Attorney, Agent, or Firm—Morgan & Finnegan

(57) ABSTRACT

A method and apparatus for imaging teeth includes illuminating a surface of a tooth and electronically imaging the tooth from a non-illuminated surface of the tooth with an electronic camera. Automatic control of the intensity of illumination is preferably provided to avoid saturation of the camera. The camera may include a charge-coupled-device and the resulting digital images are preferably enhanced by wavelet analysis. If a video camera is used, the images may be digitized and then enhanced. Current images of the tooth may be compared to prior images of the same tooth to monitor changes in the tooth over time. The images can be used to detect dental caries and other dental conditions. A handpiece for illuminating the tooth and receiving the light passing through the tooth for reception by the camera in a reproducible manner, is also described.

69 Claims, 20 Drawing Sheets

U.S. PATENT DOCUMENTS

| | | | |
|---|---|---|---|
| 4,184,175 | * 1/1980 | Mullane, Jr. | 433/29 |
| 4,265,227 | 5/1981 | Ruge | 128/23 |
| 4,286,602 | 9/1981 | Guy | 128/665 |
| 4,324,546 | 4/1982 | Heitlinger et al. | 433/25 |
| 4,385,344 | 5/1983 | Gonser | 362/32 |
| 4,413,278 | 11/1983 | Feinbloom | 358/93 |
| 4,468,197 | * 8/1984 | Provost | 433/30 |
| 4,479,499 | 10/1984 | Alfano | 128/665 |
| 4,490,433 | 12/1984 | Alfano | 128/665 |
| 4,516,195 | 5/1985 | Gonser | 362/281 |
| 4,539,586 | 9/1985 | Danna et al. | 358/98 |
| 4,575,805 | 3/1986 | Moermann et al. | 364/474 |
| 4,589,846 | 5/1986 | Annoni | 433/30 |
| 4,601,284 | 7/1986 | Arakawa et al. | 128/6 |
| 4,608,622 | 8/1986 | Gonser | 362/32 |
| 4,639,772 | 1/1987 | Sluyter et al. | 358/98 |
| 4,667,229 | 5/1987 | Cooper et al. | 358/98 |
| 4,727,416 | 2/1988 | Cooper et al. | 358/98 |
| 4,754,328 | 6/1988 | Barath et al. | 358/98 |
| 4,759,347 | 7/1988 | Ando | 128/6 |
| 4,836,206 | 6/1989 | Maxwell et al. | 128/633 |
| 4,836,782 | 6/1989 | Gonser | 433/229 |
| 4,860,094 | 8/1989 | Hibino et al. | 358/98 |
| 4,915,626 | 4/1990 | Lemmey | 433/31 |
| 4,928,691 | 5/1990 | Nicolson et al. | 128/633 |
| 4,947,245 | 8/1990 | Ogawa et al. | 358/98 |
| 5,007,837 | 4/1991 | Werly | 433/226 |
| 5,016,098 | 5/1991 | Cooper et al. | 358/98 |
| 5,049,070 | 9/1991 | Ademovic | 433/29 |
| 5,051,823 | 9/1991 | Cooper et al. | 358/98 |
| 5,052,924 | 10/1991 | Berg | 433/29 |
| 5,115,307 | * 5/1992 | Cooper et al. | 433/29 |
| 5,408,992 | 4/1995 | Hamlin et al. | 128/4 |
| 5,429,502 | * 7/1995 | Cooper et al. | 433/29 |
| 5,583,950 | * 12/1996 | Prokoski | 382/212 |

FOREIGN PATENT DOCUMENTS

| | | | |
|---|---|---|---|
| 922994 | 4/1963 | (GB) . | |
| 2 183 058 | 5/1987 | (GB) | A61B/1/24 |
| 53-45081 | 4/1978 | (JP) | A61B/1/00 |
| 61-190518 | 11/1986 | (JP) | G02B/23/26 |
| 63-267329 | 11/1988 | (JP) | A61B/1/24 |
| WO8502101 | 5/1985 | (WO) | A61B/7/00 |
| WO880769 | 10/1988 | (WO) | G02B/7/10 |

OTHER PUBLICATIONS

"Wavelets in medicine and biology", A. Aldroubi et al., Table of Contents, Preface, 1996.

"Using Computers to Diagnose and Plan Treatment of Approximal Caries Detected in Radiographs", R.C. Duncan et al., JADA, vol. 126, 1995, pp. 873–882.

"Digital Radiography", Clinical Research Associates Newsletter, vol. 19, Issue 5, May 1995; pp. 1–2.

"Image Features From Phase Congruency", P. Kovesi, University of Western Australia, Technical Report 95/4, Mar./Jun. 1995, pp. 1–30.

"Root caries", S. Liliasson, et al., The Telande Foundation, 1992, pp. 21–25.

"A comparison of bitewing radiography and interdental trans–illumination as adjuncts to the clinical identification of approximal caries in posterior teeth", A.D. Sidi et al., Diagnostic Aids, British Dental Journal, 1988.

"Comparison of fibre optic transillumination with clinical and radiographic caries diagnosis", K.W. Stephen et al., 1986; pp. 90–94.

"Accuracy of Visual Inspection, Fiber–optic Transillumination, and Various Radiographic Image Modalities for the Detection of Occlusal Caries in Extracted Non–cavitated Teeth", A. Wenzel et al., J. Dent Res., 1992, pp. 1934–1937.

"Singularity Detection and Processing with Wavelets", S. Mallat et al., IEEE Transactions on Information Theory, vol. 38, No. 2, Mar. 1992, p. 617–643.

"Optical Quantitation and Radiographic Diagnosis of Incipient Approximal Caries Lesions", E.H. Verdonschot et al., Clinical Science, Caries Res 1991; 25, pp. 359–364.

"The use of fiber optics transillumination for the detection of proximal caries", L.R. Manson–Hing, Dental Radiology, American Academy of Dental Radiology, Oral Surg., Dec. 1973, pp. 891–897.

"Transillumination of the oral cavity with use of fiber optics", J. Friedman et al., JADA, vol. 80, Apr. 1970, pp. 801–809.

"Illumination of the oral cavity", R.C. Taylor et al., JADA, vol. 74, May 1967, pp. 1207–1209.

"Transillumination in the Oral Cavity", G.R. Winter et al., Dental Digest, Mar. 1949, pp. 106–110.

"Diagnosis by Transillumination,", W.J. Cameron, Sixth Edition, Table of Contents, 1927, pp. 24–25.

"Diagnosis by Transillumination", W.J. Cameron, Fourth Edition, 1923, pp. 16–17.

"Increased spatial resolution for light images of tissues—especially for teeth", A.O. Wist et al., SPIE, vol. 1894, pp. 52–63, 1993.

"Wavelet Maxima Presentation", S. Mallat et al., Courant Institute of Mathematcial Sciences, pp. 206–284, 1989.

"Image Features From Phase Congruency", P. Kovesi, Technical Report 95/4, Department of Computer Science, The University of Western Australia, Jun. 1995; pp. 1–30.

"Singularity Detection and Processing with Wavelets", S. Mallat et al., IEEE Transactions on Information Theory, vol. 38, No. 2, Mar. 1992; pp. 617–643.

"Characterization of Signals from Multiscale Edges", S. Mallat et al., IEEE Transactions on Pattern Analysis and Machine Intelligence, vol. 14, No. 7, Jul. 1992; pp. 710–732.

Robot Vision, B. Horn et al., The MIT PRess, 1991; pp. 48–53, 175.

"The Wavelet Transform, Time–Frequency Localization and Signal Analysis," I. Daubechies, IEEE Transactions on Information Theory, vol. 36, No. 5, Sep. 1990; pp. 961–1005.

"Introduction to Statistical Pattern Recognition", K. Fukunaga, Academic Press, Inc., 1990; pp. 91–97, 124–125, 219–221.

"A Theory for Multiresolution Signal Decomposition: The Wavelet Representation", S. Mallat, IEEE Transactions on Pattern Analysis and Machine Intelligence, vol. 11, No. 7, Jul. 1989; pp. 674–692.

"Fiber Optic Lighting Systems: Their Role in Dentistry", J.L Bomba, Dental Clinics of North America, vol. 15, No. 1, Jan. 1971; pp. 197–218.

Wavelets in Medicine and Biology, A. Aldroubi et al., CRC Press, Inc., 1996; pp. 11–18.

Wavelets and Applications, Y. Meyer, editor, Springer–Verlag NY 1992; pp. 207–284, Chapter entitled "Wavelet Maxima Representation" by S. Mallat et al.

"Discover The World of Demetron", An Advertising Brochure of Demetron Research Corporation, Danbury, Connecticut; 1983.

"Handbook of Visual Communications", H. Hang et al., Academic Press, 1995; pp. 156–158.

* cited by examiner

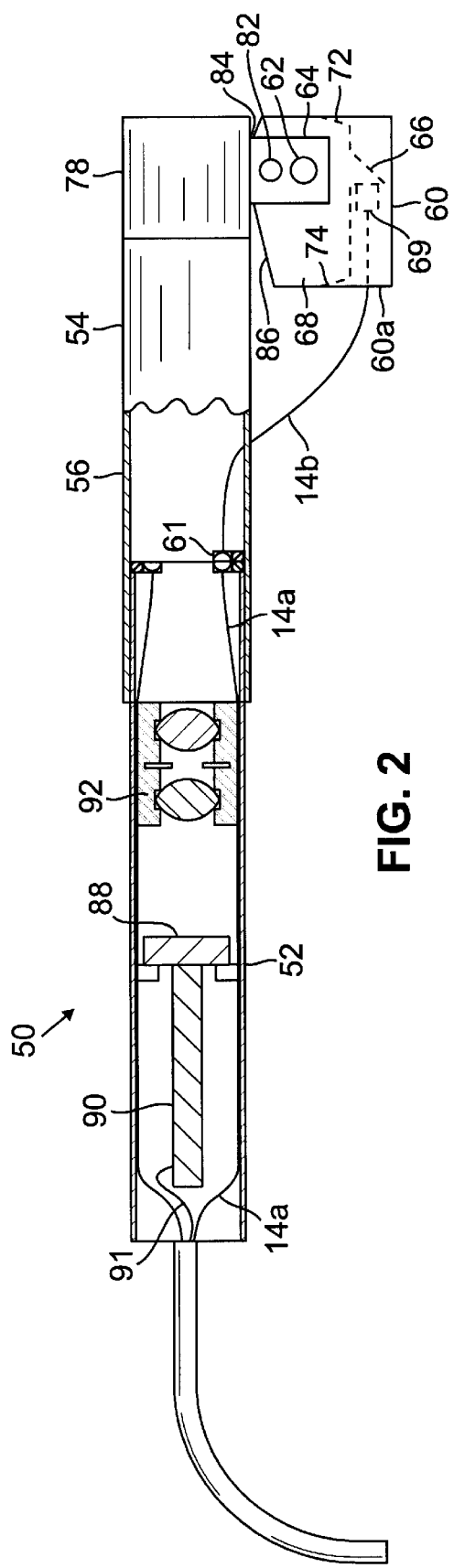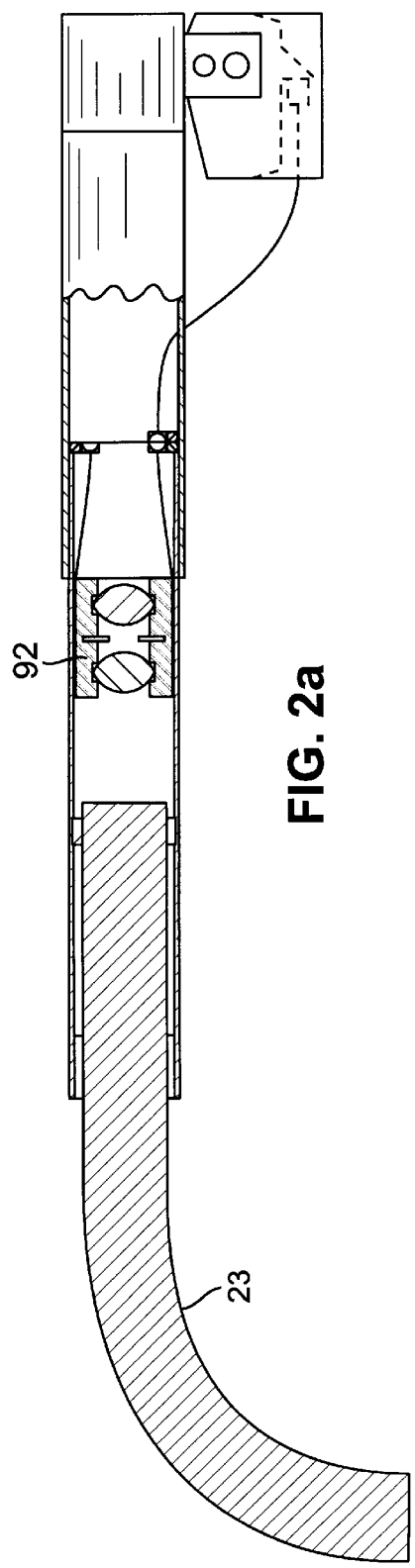
FIG. 2
FIG. 2a

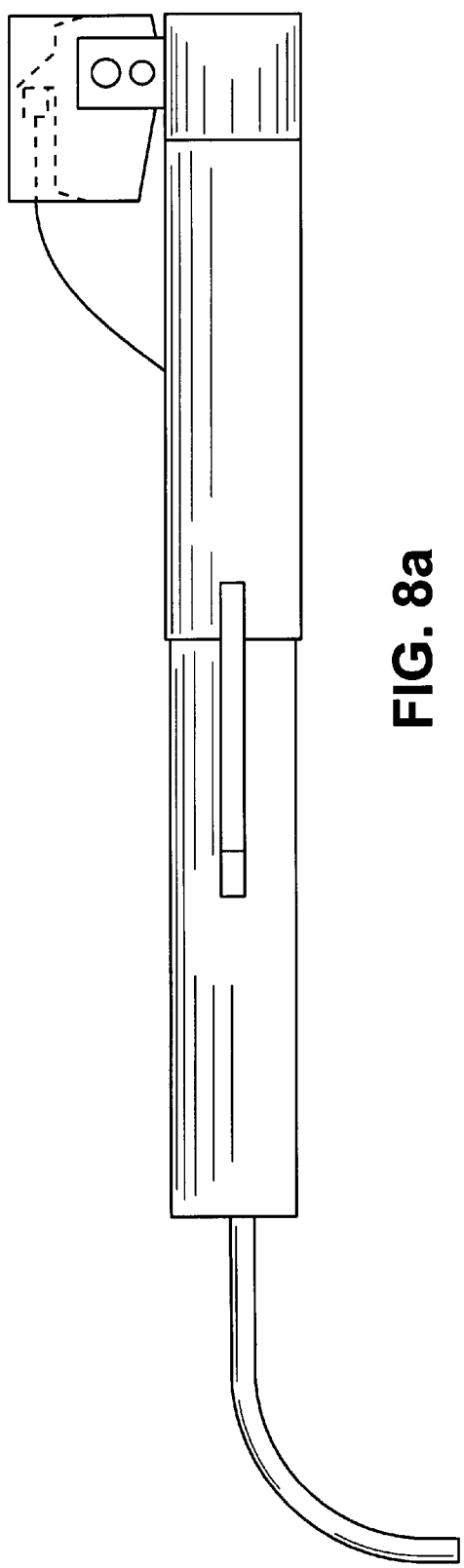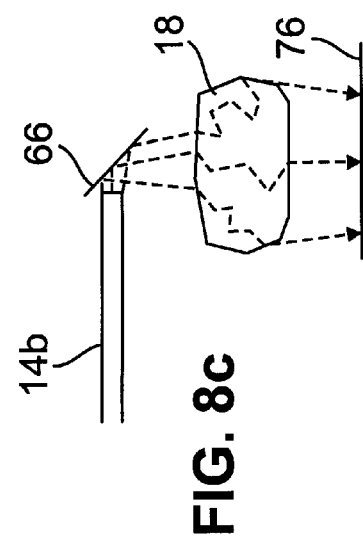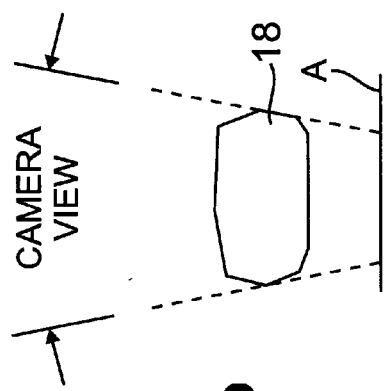

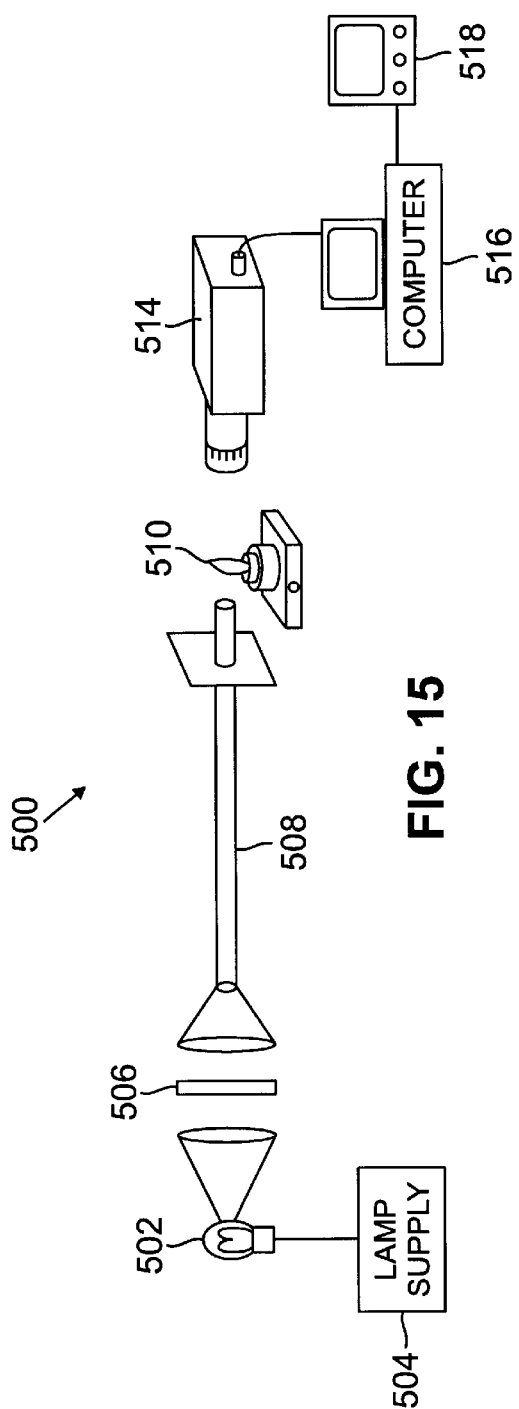
FIG. 15
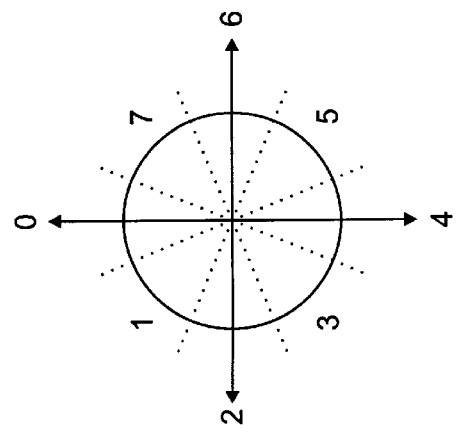
FIG. 17b
FIG. 17a

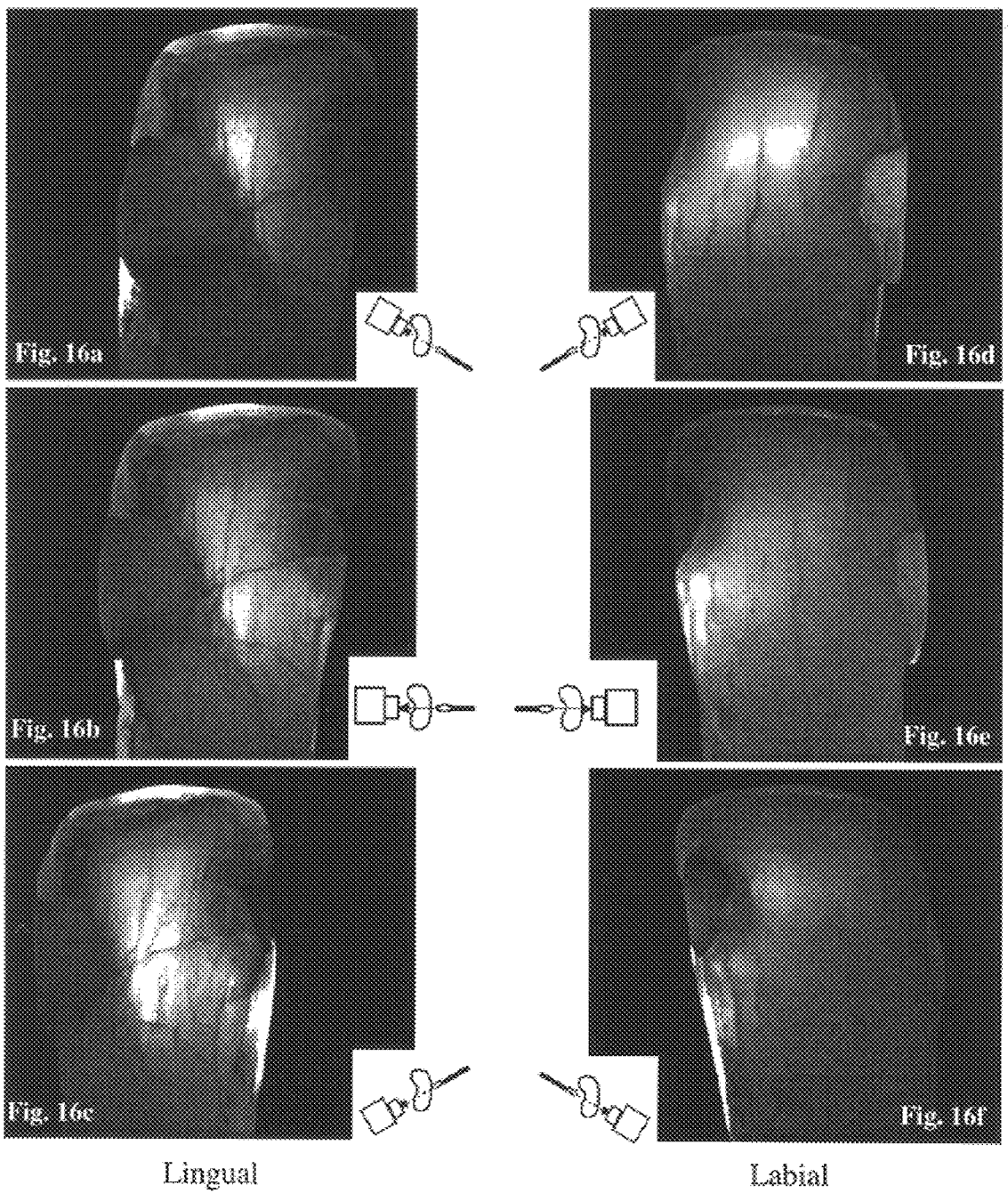

METHOD AND APPARATUS FOR ELECTRONICALLY IMAGING A TOOTH THROUGH TRANSILLUMINATION BY LIGHT

STATEMENT AS TO RIGHTS TO INVENTIONS MADE UNDER FEDERALLY-SPONSORED RESEARCH AND DEVELOPMENT

The U.S. Government has a royalty-free license to the invention pursuant to 37 CFR 401, by virtue of its partial support of research under National Institutes of Health Small Business Innovative Research Grant 1R43DE11507.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyrights whatsoever.

FIELD OF THE INVENTION

This invention relates to method and apparatus for imaging teeth. More particularly, the invention relates to illuminating a tooth with light and creating images of the illuminated tooth.

BACKGROUND OF THE INVENTION

The most commonly used clinical techniques for detecting dental caries are tactile examination and dental radiography, each of which has significant shortcomings. Tactile examination typically uses an explorer, which can accelerate the development of irreversible caries by causing traumatic changes to tooth structure. Radiography requires the use of x-ray radiation, which is an ionizing radiation dangerous to the health of the patient. The use of lower x-ray fluence with digital sensing of the x-ray transmission and computer enhancement of the image contrast, provides poorer resolution than that obtainable with x-ray film.

Another clinical technique is to visually inspect a tooth illuminated by light. Transillumination by light can indicate the presence of caries because decayed tooth material causes greater scattering of light and may provide greater absorption of light, than surrounding healthy tooth tissue. A decayed region will therefore appear darker than surrounding tissue. If the tooth has decayed sufficiently to leave a void, more light would be transmitted through the tooth.

Dental diagnosis by transillumination of teeth using visible light reportedly dates back to 1865. See, for example, G. R. Winter et al., "Transillumination in the Oral Cavity," Dental Digest 106–109 (March 1949). This technique has evolved into fiberoptic transillumination ("FOTI"), which uses fiber optics to deliver the light to the teeth. FOTI has been used by a relatively small number of dentists for caries examination since 1968. See, for example, J. Friedman and M. I. Marcus, "Transillumination of the Oral Cavity with Use of Fiber Optics," 80 J Am Dent Assoc 801–809 (Apr. 1970); J. Barenie et al., "The Use of Fiber Optics Transillumination for the Detection of Proximal Caries," 36 Oral Surg 891–897, No. 6 (Dec. 1973).

A typical FOTI apparatus employs an incandescent light source having two intensity levels for illuminating the tooth via an optical fiber bundle. The light passing through the tooth is conveyed through another fiber bundle to form an image on a ground glass screen on photographic film in a camera, or to be viewed by the eye. See, for example, U.S. Pat. No. 4,446,197 to Provost.

Heretofore, it has been difficult to obtain reliable FOTI images containing clinically significant information. Variations in the intensity, position of the illumination source, and viewing angle of the camera, for example, introduce high degrees of variability to FOTI images, impeding FOTI's practical implementation. It is difficult to obtain identical FOTI images of even the same tooth a second time. It is therefore difficult to compare current FOTI images with prior FOTI images to monitor changes in the tooth over time. It is also difficult to develop standards by which to determine whether or not caries is present based on FOTI images. Unless FOTI can dependably and reproducibly yield images with clinical content of interest, it is likely to remain a rarely used clinical technique. See, for example, K. W. Stephen, et al.; "Comparison of fiber optic transillumination with clinical and radiographic caries diagnosis," 15 Comm Dent Oral Epidemiol 91–94 (1987); A. D. Sidi, M. N. Naylor, "A comparison of bitewing radiography and interdental transillumination as adjunct to the clinical identification of approximal caries in posterior teeth," 164 Brit Dent J 15–17 (1988); and S. Eliassen, et al., "Root caries: a consensus conference statement," 16 Swed Dent J 21–25 (1992).

While several methods of providing reproducible results have been proposed, none appears practical. For example, in one reported variant of FOTI, a collimated light source and a scanning detector are employed. See, for example, A. O. Wist, et al., "Increased spatial resolution for light images of tissues especially for teeth," 1894 SPIE 52–64 (March 1993). Such a configuration suffers from poor light efficiency and lacks sufficient flexibility for routine clinical use. None of the known versions of FOTI reported to date provides the degree of control over the imaging conditions that is necessary for adequate quality and reproducibility of results.

SUMMARY OF THE INVENTION

The present invention minimizes the sources of variability in imaging conditions which prevent adequate light imaging of a tooth and impede the reproducibility of images of the tooth, improving the capture of clinically significant information. For example, an electronic camera, such as a camera incorporating a charge-coupled-device ("CCD") or a video camera, is used to image the illuminated tooth. Electronic imaging, particularly with a CCD, enables real time observation of the tooth under a variety of conditions so that the operator can capture a frame of interest for further processing and review in near real time. A CCD is preferred because of its high signal-to-noise ratio. The intensity of the illumination source is preferably automatically controlled to determine the optimum intensity for imaging the tooth, while avoiding saturation of the camera. The range of intensities may then be linearly mapped into a standard range for image representation, providing improved image contrast and resolution. The angle of reception by the camera of the light passing through the tooth may also be controlled in a reproducible manner. The images may be digitized and subjected to digital processing. Wavelet transformations have been found to provide particular improvement in the sensitivity and robustness of the image.

In accordance with the present invention, a method of acquiring images of a tooth comprises illuminating a surface of the tooth with light radiation and electronically imaging the tooth from a non-illuminated surface. The electronic imaging can be conducted by an electronic camera, which preferably includes a CCD, or by a video camera. Preferably, the illuminating step and the imaging step are sequentially conducted a plurality of times and the intensity of the light radiation is automatically adjusted to avoid saturation of the camera. At least some of the imaging steps are conducted at different angles with respect to the tooth. If the electronic camera includes a CCD, the resulting digital images are preferably enhanced by representing the image through wavelet amplitude maps, wavelet phase maps, or both. If the camera is a video camera, the images may be digitized and then enhanced.

A current image of the tooth may be compared to a previously taken image of the same tooth to identify changes in the tooth over time through a numerical correlation, for example.

A plurality of teeth may be illuminated and imaged based on light reflected from the teeth, as well.

Also in accordance with the present invention, a system for acquiring images of a tooth by transillumination is disclosed comprising an illuminator source for illuminating the tooth, an electronic camera, means for transferring light passing through the tooth to the camera, a digital processing unit coupled to the electronic camera, and a monitor for displaying images, coupled to the digital processing unit. The illuminator source may be a high intensity lamp connected to an optical fiber for illuminating a surface of a tooth of interest. A small laser, a laser diode, a light emitting diode, or a miniature light bulb may also be used as the source of illumination, as well. The electronic camera may include a CCD or may be a video camera. Provision is preferably made for automatically changing the intensity of the light to avoid saturation of the camera by means, such as a digital processing unit, coupled to the illuminator and to the camera. The means for transferring light may include one or more mirrors for reflecting light passing through the tooth to a lens assembly, which focuses the light onto the camera. A handpiece is also preferably provided for being positioned proximate the tooth wherein the camera, the means for transferring light and the illuminator source are part of the handpiece. The handpiece engages selected surfaces of the teeth to establish a frame of reference enabling repeatable illumination and imaging of the tooth with respect to the frame of reference.

If the camera includes a CCD, the resulting digital images are preferably enhanced by the digital processing unit by representing the image through wavelet amplitude maps, wavelet phase maps, or both. If the camera is a video camera, the resulting images may be digitized and then enhanced.

The digital processing unit, which can be a computer, also preferably compares a current image of a tooth to a previously taken image of the same tooth to identify changes in the tooth over time, by using some form of numerical correlation, for example.

The system may also include an illumination source for illuminating a plurality of teeth and means for transferring light reflected from the teeth to a camera for imaging, as well.

In another embodiment of the invention, an apparatus for illuminating a tooth of interest has a handle having a front end and a horizontal plate for resting on an occlusal or incisal surface of the tooth. The plate is preferably rotatably coupled to the front end. The horizontal plate has a first edge proximate to the front end and a second edge distanced from the front end. A vertical wall depends perpendicularly from the second edge, perpendicular to the horizontal plate and a first prong extends from an edge of the vertical wall towards the front end, for bearing against an a proximal surface of the tooth. A means for illuminating the tooth, such as an optical fiber coupled to an illumination source, a small laser, a laser diode, a light emitting diode, or a miniature light bulb, for example, is located within the vertical wall adjacent to the first prong. A means for receiving the light passing through the tooth depends from the front end, opposite to the illuminating means and distanced from the illuminating means a sufficient distance for the tooth to be received therebetween. The means for receiving light can be one or more mirrors, for example. A second prong is preferably provided extending from the vertical wall, on an opposite side of the illumination means as the first prong. A camera, which can include a CCD, may be located within the handle. The apparatus can be reproducibly positioned with respect to a tooth, and thereby enables reproducible imaging of the tooth.

BRIEF DESCRIPTION OF THE DRAWINGS

FIG. 2 is a partial cross-sectional top view of a handpiece in accordance with another embodiment of the invention, for use with the system of FIG. 1;

FIG. 2a is a partial cross-sectional top view of a handpiece wherein an optical fiber is provided within the handpiece for transferring light to a camera;

FIGS. 7a, 8a and 9a are top views of the handpiece, with its illumination section rotated to the left, in an intermediate position and rotated to the right;

FIGS. 7b, 8b and 9b show the different views of the tooth by the camera, when the illumination section is in the positions of FIGS. 7a, 8a and 9a, respectively;

FIGS. 7c, 8c and 9c show the position of the second mirror with respect to the tooth when the illumination section is in the positions of FIGS. 7a, 8a and 9a, respectively;

FIG. 15 is a schematic representation of the laboratory apparatus used to demonstrate the present invention;

FIGS. 16a–16f are a series of lingual and labial images of a tooth obtained with the laboratory apparatus of FIG. 15, each having an inset showing the angle of illumination and reception with respect to the tooth;

FIG. 17a is a direction matrix used in the wavelet segmentation of the tooth of interest;

FIG. 17b illustrates the translation of the angle of the x and y components to the direction matrix of FIG. 17a;

FIG. 20b is a graph of line scans across a lesion at the positions indicated by thin white lines in the three left panels in FIG. 20a;

FIG. 22b shows the boundary resulting from the segmentation of the images of FIG. 22a;

FIG. 23b is a plot of the standard deviation of the NCC values at the same grid points as in FIG. 23a;

FIG. 24b is a 3-dimensional plot of NCC vs. intensity and resolution, comparing the original image of FIG. 24a with the intensity reduced image of FIG. 24a.

DETAILED DESCRIPTION OF THE INVENTION

Figure 1:
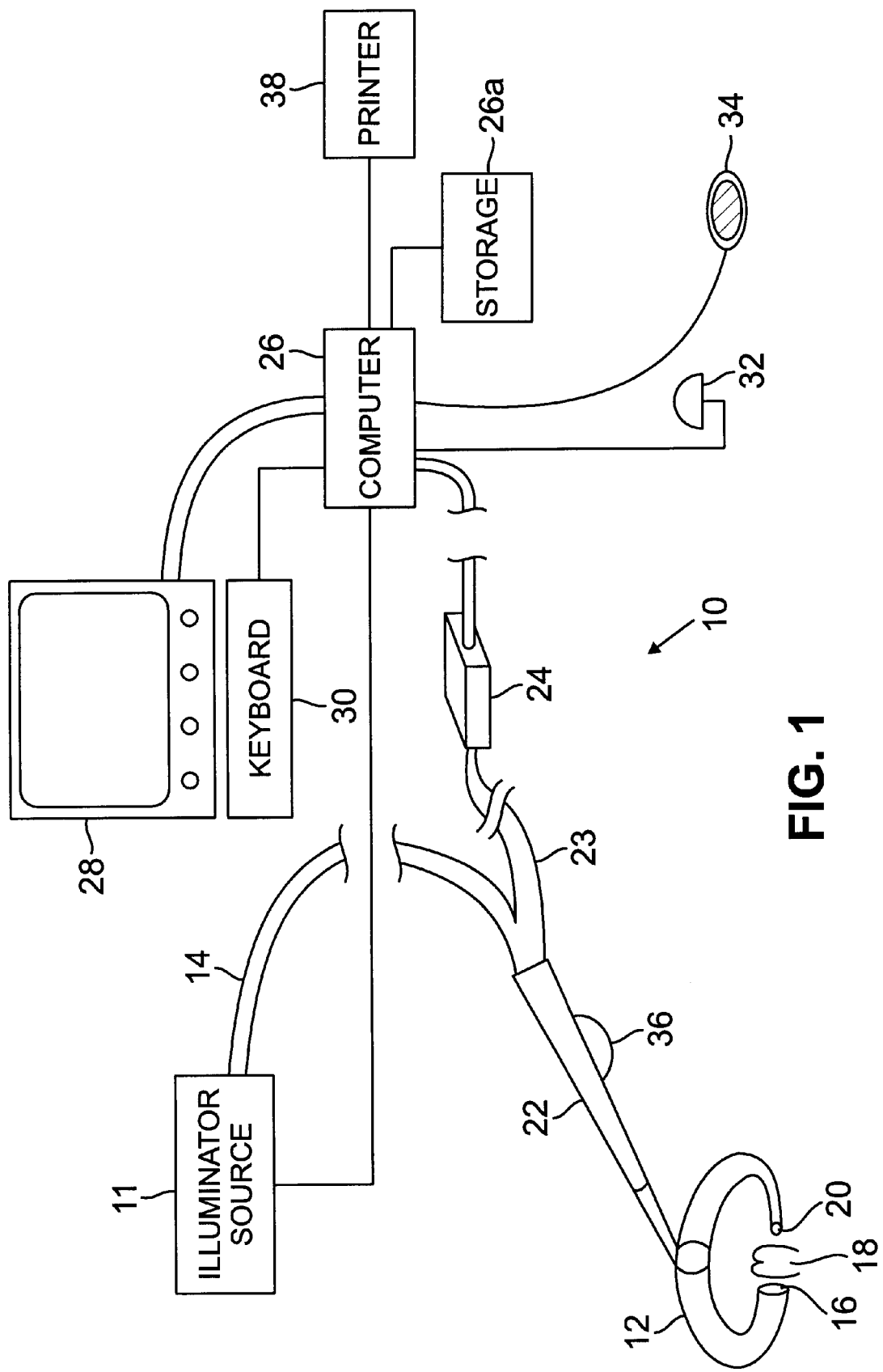
FIG. 1 is a schematic representation of an apparatus for imaging teeth in accordance with one embodiment of the present invention.

FIG. 1 schematically illustrates the principal components of a system 10 for imaging teeth in accordance with one embodiment of the present invention. The preferred embodiment of the system 10 is referred to as a digital imaging fiber optic transillumination system ("DIFOTI™"). The system 10 includes a source of illumination 11 which provides light to a handpiece 12 via an optical fiber or optical fiber bundle 14. The handpiece 12 has an output portion 16 from which light exits the handpiece 12 for illuminating a tooth 18 under examination, and an image input portion 20 for receiving light passing through the tooth. The output portion 16 and image input portion 20 of the handpiece 12 define a region therebetween for receiving the tooth 18. A preferred handpiece in accordance with the present invention is described, below.

The image plane of an electronic camera 24 may be optically coupled to the image input portion 20 of the handpiece 12 through a separate optical fiber or fiber optic bundle 23. Preferably, the camera is a digital electronic camera having a charge-coupled-device (CCD) imaging array coupled to the optical fiber 23. The CCD may be located within the handpiece 12 as well, as discussed with respect to the embodiment of FIG. 2. A CCD is preferred because of its high signal-to-noise ratio and its direct generation of digital signals for immediate processing. An intra-oral camera could also be positioned in the mouth, adjacent the side of the tooth opposite the side being illuminated. Alternatively, a video camera may be used and the video images subsequently digitized.

The camera 24 has an output for providing the images to a computer 26. The computer 26 is connected to a monitor 28, such as a cathode ray tube (CRT) or liquid crystal display monitor. A keyboard 30, a mouse 32, a foot control 34 and/or a hand control 36, are preferably connected to the computer 26 for inputting data and controlling the computer 26, as discussed further, below. A hard-copy terminal such as a printer 38 is preferably provided connected to the computer 26, as well. The hand control 36 is preferably provided on the handle 22 of the handpiece 12.

The computer 26 preferably has at least a 40 MHz clock speed and 16 megabytes of random access memory. An i486 Personal Computer, or its equivalent, may be used, for example. More advanced processors may be used, as well. The monitor 28 can be a standard 14 inch monitor with gray scale format, for example.

The illuminator source 11 is a high intensity light source, such as a 24-watt metal halide short arc lamp. The intensity of the lamp is preferably controlled by an adjustable, stabilized power supply. A suitable lamp is an EXP0794 from Welch Allyn Corp., Lighting Products Division, Skaneateles Falls, N.Y. 13153, for example. A 50 watt version of the EXPO794 may be used, as well. Other high intensity light sources, such as a small laser, a laser diode, a light emitting diode ("LED"), or a miniature light bulb, for example, may also be used to provide light for illuminating the tooth through the optical fiber 14 or directly by being positioned within the handpiece 12.

Interference filters are preferably provided to define one or more selectable spectral bands of illumination. The filters may be provided on a filter wheel (not shown), for example. Four wavelength bands are preferred, centered at 500 nm, 600 nm, 700 nm and white light. The power supply of the illuminator source 11 and the filter wheel are preferably coupled to the computer 26 so that the intensity and wavelength of the light can be adjusted. Other methods of adjusting the intensity of the light, such as through filters, may be used as well. Different wavelength bands provide different contrasts, which have been found to improve the identification of caries or other conditions.

Adjustment of the intensity of the light illuminating the tooth is advantageous because the varying thickness and density of different types of teeth, require different degrees of light intensity for optimal illumination and analysis. In addition, the intensity of light can be adjusted to avoid saturation of the CCD. Preferably, the intensity is continuously adjustable over a range.

The optical fibers 14 and 26 can each be a single fiber with an aperture on the order of 1 mm or less, for example. The fiber used in laboratory demonstrations had a 0.365 mm aperture, 0.22-NA. A multi-fiber bundle with a 3 mm aperture, for example, may be used, as well. The fiber 26 should be an image preserving fiber or bundle. The fiber can be a autoclavable part or it can be provided with a thin, disposable, plastic sheath. Preferably, less than the entire side of the tooth is illuminated, to avoid reception of light passing around the tooth. Such light does not provide useful information.

The camera 24 may be a Toshiba ½" Model IK-541P-A high resolution CCD (720×570 pixels), equipped with a 23 mm Schneider f/1.4 Xenoplan lens and an extender for reducing the field of view ("FOV"), for example. The image calibration scale was 43 pixels/mm over a 11.5 mm FOV. Smaller cameras are available, such as Toshiba's ⅓" IK-LTM42A Camera. A video camera may also be used, in which case the video image would need to be digitized prior to its being provided to the computer processor.

The printer 38 may be a low cost, hard copy printer, such as a commercially available 600 dots per inch (dpi) laser printer, for example. Output may also be provided in pseudocolor at a resolution that is compatible with existing inexpensive color inkjet printers, such as 360×720 or 720× 720 dpi. With either type of output, hardcopies can be generated at any time from stored image files.

An auxiliary storage device 26a, such as a floppy disc drive, a tape drive, ZIP drive, JAZ drive, or WORM drive, is preferably coupled to the computer 26 for storage of the images.

Figure 3:
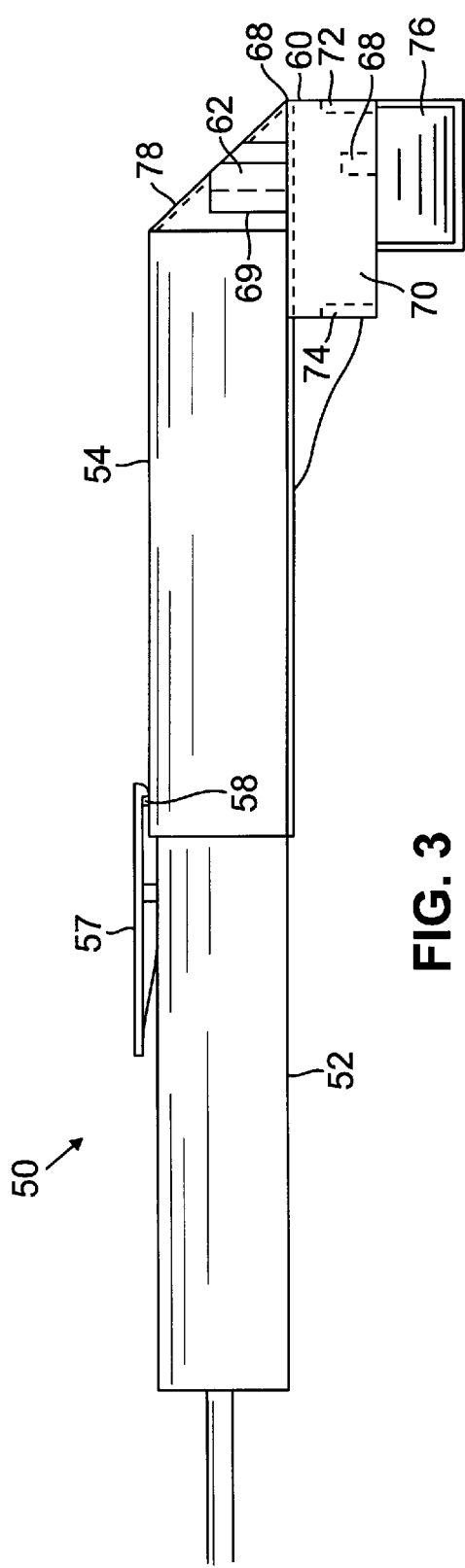
FIG. 3 is a side view of the handpiece of FIG. 2.
Figure 4:
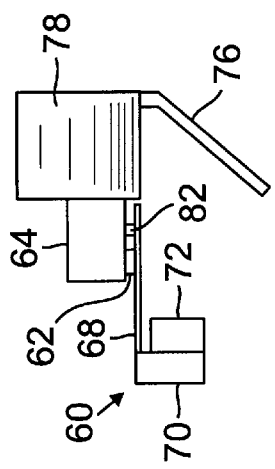
FIG. 4 is a front view of the distal portion of the handpiece 50 of the view of FIG. 3.
Figure 6A:
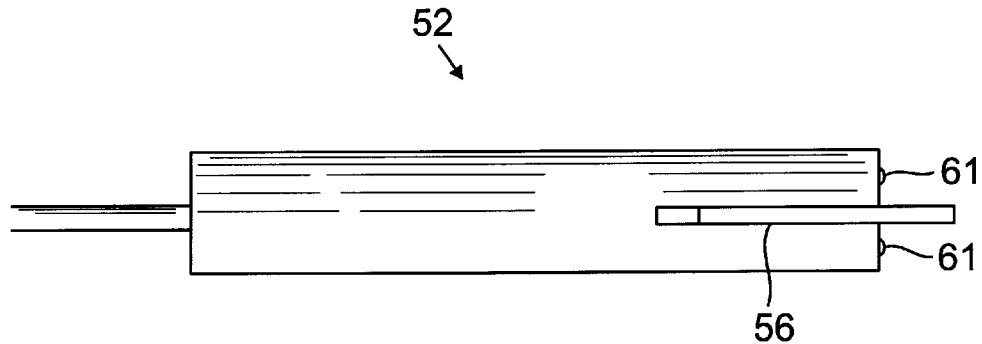
FIG. 6a is a side view of the handle separated from the handpiece.
Figure 6B:
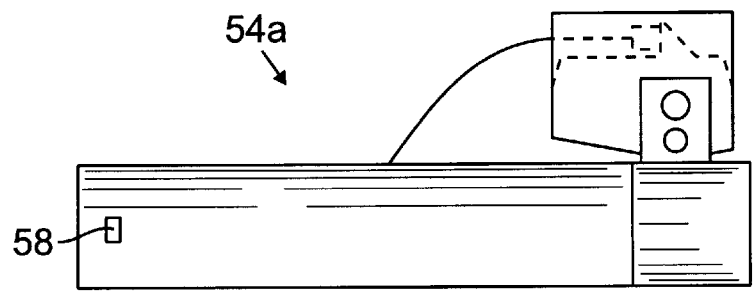
FIGS. 6b–6c are each top views of two mouthpieces, which are mirror images of each other, for imaging all of the teeth of the mouth.
Figure 6C:
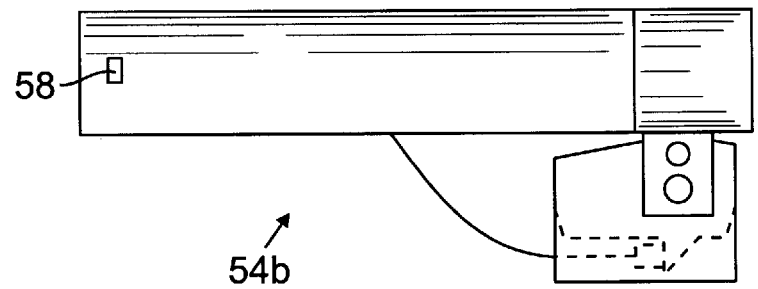

FIG. 2 is a partial cross-sectional top view of a handpiece 50 in accordance with another embodiment of the invention, for use with the system of FIG. 1. FIG. 3 is a side view of the handpiece 50 of FIG. 2, and FIG. 4 is a front view of the distal portion of the handpiece 50 of the view of FIG. 3. The handpiece 50 preferably comprises two separable parts, a handle 52 and a mouthpiece 54. FIG. 6a is a side view of the handle 52 separated from the mouthpiece 54. FIGS. 6b and 6c are each top views of two mouthpieces 54a, 5b, respectively, which enable imaging all of the teeth of the mouth. When attached to the handle 52, the mouthpiece 54a of FIG. 6b enables imaging of the buccal surfaces of the teeth in the upper right and lower left quadrants and the lingual surfaces of teeth in the lower right and upper left quadrants, as viewed by the operator. The mouthpiece 54b of FIG. 6c, which is a mirror image of the mouthpiece 54a of FIG. 6b, enables imaging of the lingual surfaces of teeth in the lower right and upper left quadrants.

Returning to FIG. 2, the handle 52 is received within a tubular portion 56 of the mouthpiece 54. The outer diameter of the handle 52 and the inner diameter of the tubular portion 54 are dimensioned to provide a tight fit. Preferably, the handle 52 has a slightly inwardly tapered portion at its distal end for engaging the inner surface of the tubular portion 54. A detent mechanism such as a releasable clip 57 may be provided in the handle 52 for engaging a protrusion 58 in the tubular portion 56, shown in FIGS. 6b and 6c, to secure the handle to the mouthpiece 54. While described as tubular, the mouthpiece 54 and the handle 52 can have other shapes.

The optical fiber or bundle 14, shown in FIG. 1, has a section 14a extending through the handle 52 (shown in FIG. 2), which is coupled to a section 14b extending through a rear portion of the tubular portion 56. The section 14b exits the tubular portion 54 near its front end. An illumination section 60 is provided, preferably pivotally coupled to the front end of the tubular portion 56. A pin 62 extends from a block 64 attached to or integral with the side of the front end of the tubular portion 56, for attachment to the illumination section 60, as shown in FIG. 4. The front of the section 14b of the optical fiber 14 enters the illumination section 60 through a hole 60a. The output of the section 14a and the input of the section 14b each has a lens 61. The lenses 61 are aligned when the two sections are connected, as is known in the art. There are two sections 14a in the handle 52, for accommodating each of the optical fiber sections 14b of each mouthpiece 54a, 54b (shown in FIG. 6a).

The illumination section 60 includes a first mirror 66 positioned opposite the output 69 of the optical fiber 14b, at an angle of 135° with respect to the longitudinal axis of the optical fiber 14b. The mirror and portion of the optical fiber 14b within the illumination section 60 are shown in phantom in FIG. 2.

As mentioned above, an LED, a small laser, a laser diode or a miniature light bulb, for example, may also be used to illuminate the tooth. Those sources could provide illumination through the optical fiber 14, they could be positioned adjacent the first mirror 66, or they could be positioned to directly illuminate the tooth, dispensing with the need for the first mirror 66. In any case, as mentioned above, it is preferred that less than the entire side of the tooth be illuminated to avoid reception of light passing around the tooth of interest. Preferably, the illumination is directed at or near the center of the lingual or buccal surface of the tooth.

The illumination section 60 includes a horizontal plate 68 which is connected to the block 64 by the pin 62. A vertical wall 70 depends from an edge of the horizontal plate 68, as shown in FIGS. 3 and 4. The first mirror 66 is provided within the vertical wall 70. Front and rear vertical prongs 72, 74 extend from the edges of the vertical wall 70, perpendicular to the vertical wall 70 and to the horizontal plate 68. The prongs 72, 74 are shown in phantom in FIGS. 2 and 3, and in cross-section in FIG. 10. The front prong 72 is shown in FIG. 4. The prongs may have a height of 0.25 inches, a width of 0.15 inches and a thickness of 0.015 inches, for example.

Figure 5:
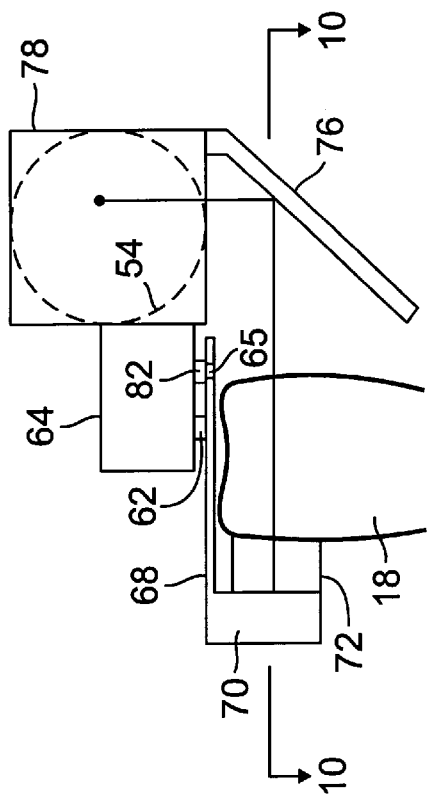
FIG. 5 is an enlarged front view of the distal portion of the handpiece of FIG. 3, positioned over a tooth of interest.

The tubular portion 56 of the mouthpiece 54 includes a second mirror 76 depending from its front end in a plane angled 45° with respect to the plane of the horizontal plate 68 in FIG. 4. A third mirror 78 is mounted within the front end of the tubular portion 56, in a plane angled 45° with respect to the horizontal plate 68 in the view of FIG. 3. The front end may be square, elliptical or round. The first mirror 66 is oriented to reflect light output from the optical fiber 14b towards the second mirror 76, which is oriented to reflect the light to the third mirror 78, which is oriented to reflect the light down the tubular portion 56. As shown in FIG. 5, for example, a tooth 18 under examination is positioned between the first mirror 66 (in the vertical wall 70) and the second mirror 76. It is understood that other mirror arrangements are possible.

A spring loaded ball 82 or other such mechanism is preferably provided in the block 64 for engaging a depression or hole 65 in the horizontal plate 68, to lock the illumination section 60 into an intermediate position with respect to the tubular portion 54, as shown in FIGS. 4 and 5.

Figure 7A:
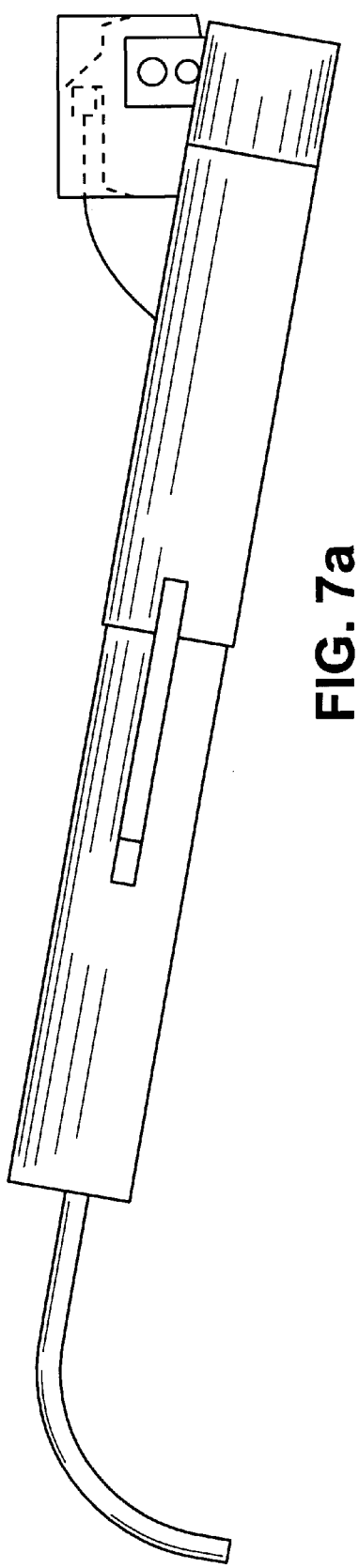
Figure 9A:
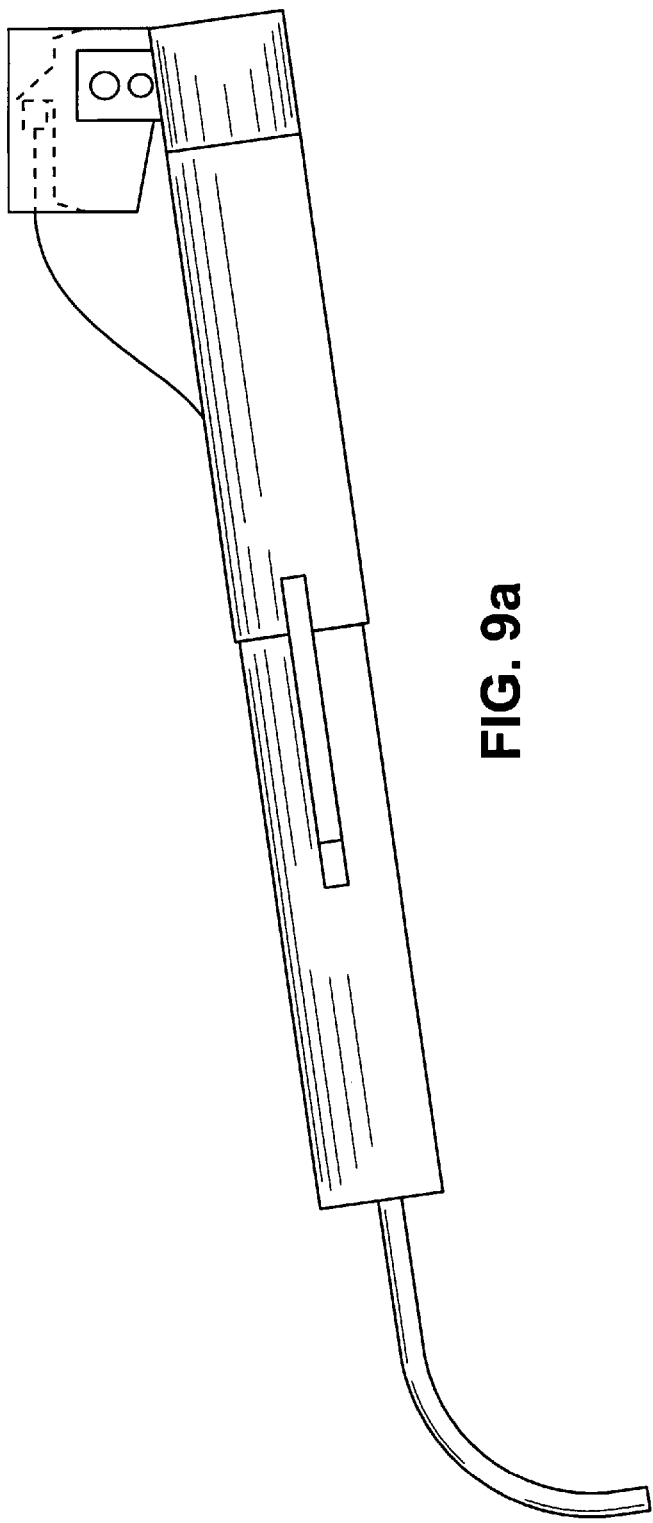

The side of the horizontal plate 68 adjacent the tubular portion 56 has two portions 84, 86 which are angled away from the tubular portion 56 to allow for rotation about the pin 62. The two portions 84, 86 provide stopping surfaces limiting the degree of rotation of the tubular portion 56 of the mouthpiece 54 with respect to the illumination section 60. 10° rotation in either direction is preferred. Three positions are therefore defined, an intermediate position where the hole is engaged, as shown in FIGS. 2 and 8a, and two positions plus and minus 10° from the intermediate position, wherein the tubular portion is rotated with respect to the illumination section 60, as shown in FIGS. 7a and 9a. Positions between the stop positions can be used, as well.

Returning to FIG. 2, the CCD 88 of the electronic camera 24 is preferably located in the handle 52 of the handpiece 50. The CCD 88 is mounted to a printed circuit board 90 and a wire 91 for coupling the CCD 88 and circuit board 90 to the computer 26. A lens assembly 92 is provided for focusing the light reflected from the third mirror 78, onto the CCD 88. Two lenses are shown, as an example. The clip 57 and the protrusion 58 are arranged such that when the protrusion 58 of the tubular portion 56 is positioned to be engaged by the clip 57, the third mirror 78 is properly aligned with respect to the lens assembly 92.

If the CCD 88 is located outside the handpiece 52, as shown in FIG. 1, the lens assembly 92 could focus the light into the optical fiber or bundle 23, which could transfer the light to the CCD camera 24, as shown in FIG. 2a.

The handle 52 and mouthpiece 54 may be easily molded of styrene, for example. The mirrors may be aluminized styrene, for example. The components of the mouthpiece 54, particularly the mirrors 66, 76 and 86, are relatively inexpensive. It is preferred that they be disposed after use, avoiding the need to clean and sterilize the mouthpiece 54 for reuse. Expensive components of the handpiece 50, such as the CCD 88 and lens assembly 92 are preferably part of the handle 52, which is reused.

Figure 9C:
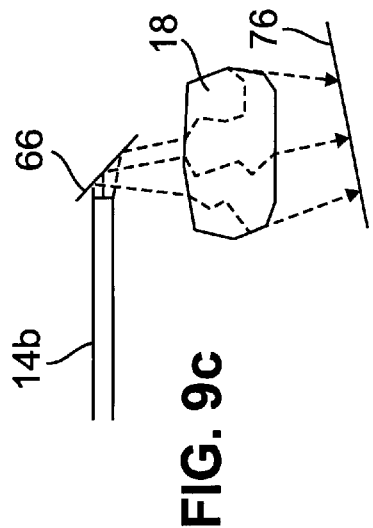
Figure 9B:
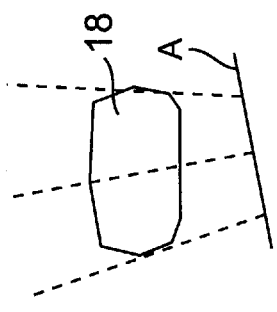
Figure 10:
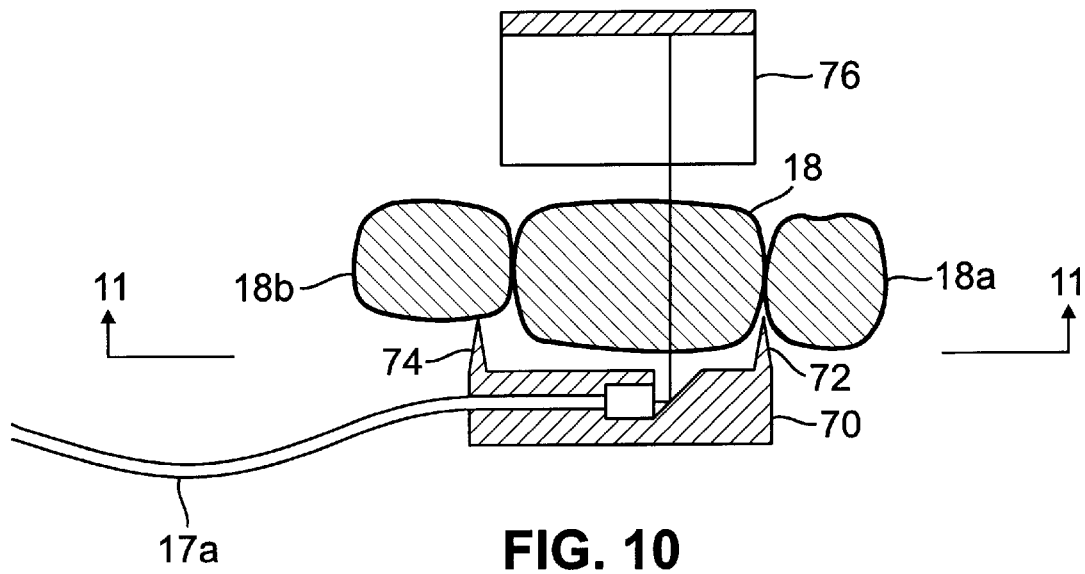
FIG. 10 is a cross-sectional view of FIG. 5 taken along line 10—10, showing the relation between the prongs, the tooth of interest, and the adjacent teeth.
Figure 11:
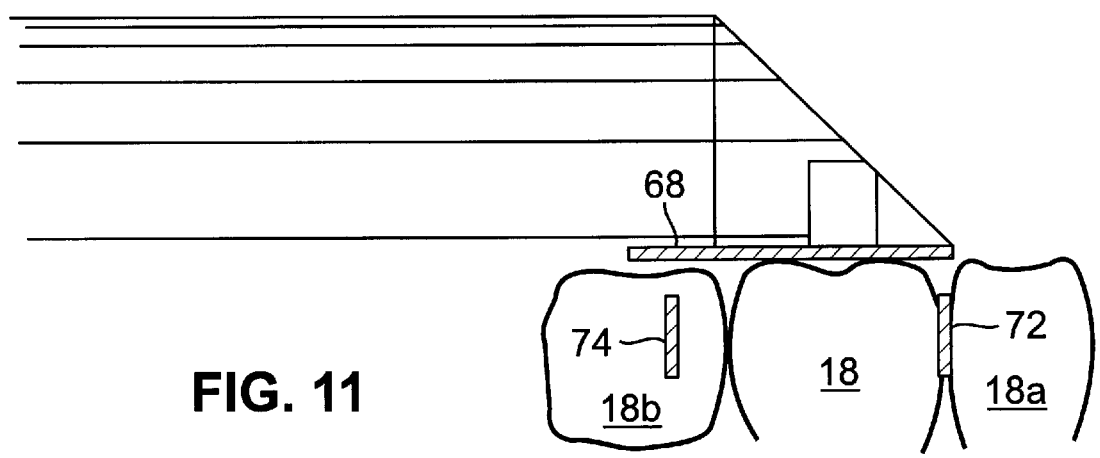
FIG. 11 is a cross-sectional view of the tooth of interest and adjacent teeth taken along line 11—11 in FIG. 10, showing the prongs and the horizontal plate in cross-section to further illustrate their position with respect to the teeth.

Use of the handpiece 50 will be discussed with respect to FIGS. 5, 7a–c, 8a–c, 9a–c, 10 and 11. The handpiece 50 is positioned over a tooth of interest 18 such that the horizontal plate 68 rests on the occlusal or incisal surface of the tooth 18, as shown in FIG. 5. FIG. 10 is a cross-sectional view of FIG. 5 along line 10—10, showing the relation between the prongs 72, 74, the tooth of interest 18 and the adjacent teeth 18a, 18b. The front prong 72 is typically inserted between the tooth of interest 18 and the adjacent tooth 18a such that the front prong 72 bears against the proximal surface of the tooth 18. The rear prong 74 is separated from the front prong 72 by a sufficient distance such that the rear prong bears against the buccal or lingual surface of the adjacent tooth 18b. A distance of about 4 mm is preferred for adults while a distance of about 2 mm is preferred for children. FIG. 11 is a side view of the tooth 18 and adjacent teeth 18a, 18b, showing the prongs 72, 74 and horizontal plate 68 in cross-section to further illustrate their position with respect to the teeth 18, 18a and 18b. If the tooth 18 is wider than the interprong spacing, if an adjacent tooth is missing or there is no adjacent tooth, as in the case of the last molar, one or both prongs 72, 74 can straddle the tooth of interest 18.

Figure 7C:
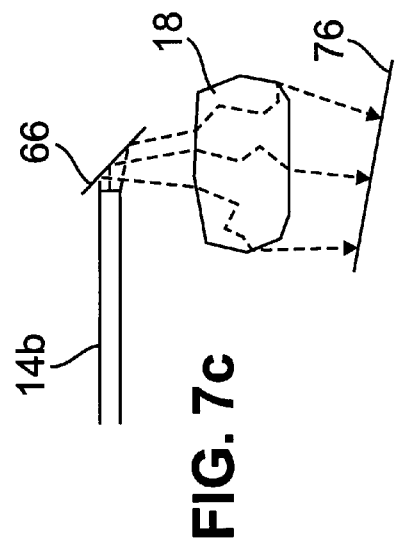
Figure 7B:
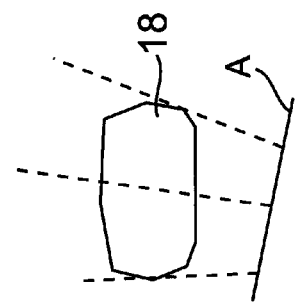

FIGS. 8a, 7a and 9a show the handpiece 50 in its intermediate position, rotated to the left and rotated to the right, respectively. FIGS. 8b, 7b and 9b show the different views of the tooth 18 by the camera, in each position. Line A in FIGS. 7b, 8b and 9b represents the image plane of the camera. FIGS. 7c, 8c and 9c show the position of the second mirror 76 with respect to the tooth 18 in each position, and examples of light rays impinging on the mirror 76. The outlines of the teeth are shown schematically in the Figures. The light rays shown schematically in FIGS. 7c, 8c and 9c experience multiple scattering as they pass through the tooth 18. Not all the light rays are scattered as they are transmitted through the tooth. The first mirror 16 and optical fiber 14b are also shown.

The mouthpiece 54 may also be readily adapted for imaging the tooth with respect to the occlusal or incisal surface of the tooth, while illuminating the buccal or lingual surface of the tooth. The handpiece 50 may include a bend to facilitate convenient movement within the oral cavities.

Figure 12:
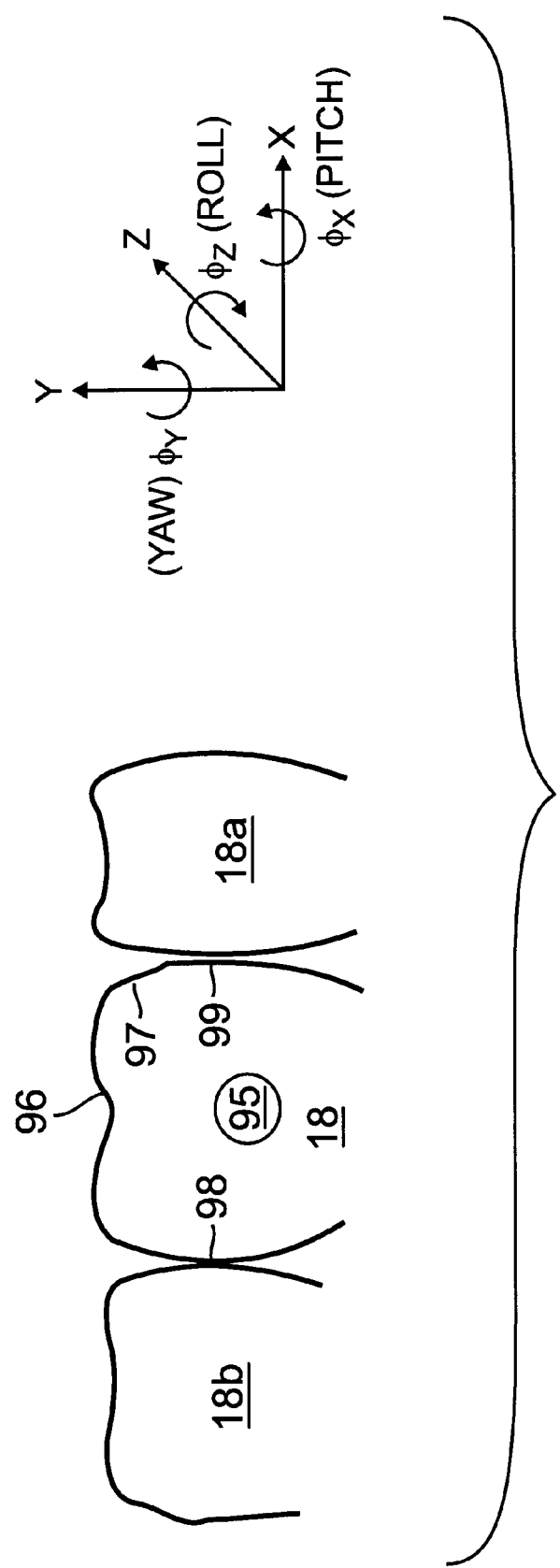
FIG. 12 is a coordinate system established with respect to the principal surfaces of the tooth of interest and showing reference points on the tooth.

The handpiece 50 of this embodiment of the invention enables the accurate reproducibility of six degrees of freedom associated with the image of a tooth of interest 18, defined with reference to the coordinate system shown in FIG. 12. Although the tooth 18 is depicted in relation to two adjacent teeth in FIG. 12, the coordinate system also applies to a single tooth in isolation. Translations are described in a right-handed Cartesian x-y-z system, in which the z-axis proceeds into the x-y plane of the figure. The x-y plane is tangent to the lingual or buccal surface, whichever is closer to the observer, at point 95. Positions along the y-axis are defined relative to an apical point 96, which is located on the occlusal or incisal surface of the tooth 18. Positions along the x-axis are defined relative to a margin of the tooth 18, which is defined by the outermost point at the tooth, such as point 97. If the outermost point is obscured by an adjacent tooth, the margin is defined by a reference line drawn through a pair of points within the tooth 18 and adjacent to the neighboring tooth 18a such as 97 and 99. Rotations are described by roll, pitch and yaw angles, defined as follows: The roll axis is identical to the z-axis, so that roll angles are denoted by $\phi_z$. Pitch angles $\phi_x$ are taken about an axis defined by points located on opposite margins of the tooth 18 such as 98 and 99. Yaw angles $\phi_y$ are taken about the y-axis, defined by points 97 and 99, as described above.

When the horizontal plate 68 is placed on the occlusal or incisal surface of the tooth 18, and one of the prongs 72, 74 bears against the proximal surface of the tooth 18, the position of the mouthpiece 54 is reproducibly fixed in the x-y plane. The preferred second prong for bearing on the lingual or buccal surface of the tooth reproducibly fixes the position of the mouthpiece 54 with respect to the z-axis, as well. Rotation of the illumination section 60 about the pin 62 through the positions shown in FIGS. 7a, 8a and 9a provides rotation in yaw about the y-axis. If the second prong is not provided, the vertical wall itself can be used to fix the position of the mouthpiece 54 with respect to the z axis. The handpiece of the present invention thereby enables the mouthpiece 54 to be precisely placed in essentially the same position with respect to the same tooth at a later time, enabling reliable examination of the tooth and comparisons with prior images of the same tooth taken at different times. Such comparisons are useful for monitoring changes in the condition of the tooth. The second prong is particularly preferred if such comparisons are to be made.

Figure 13:
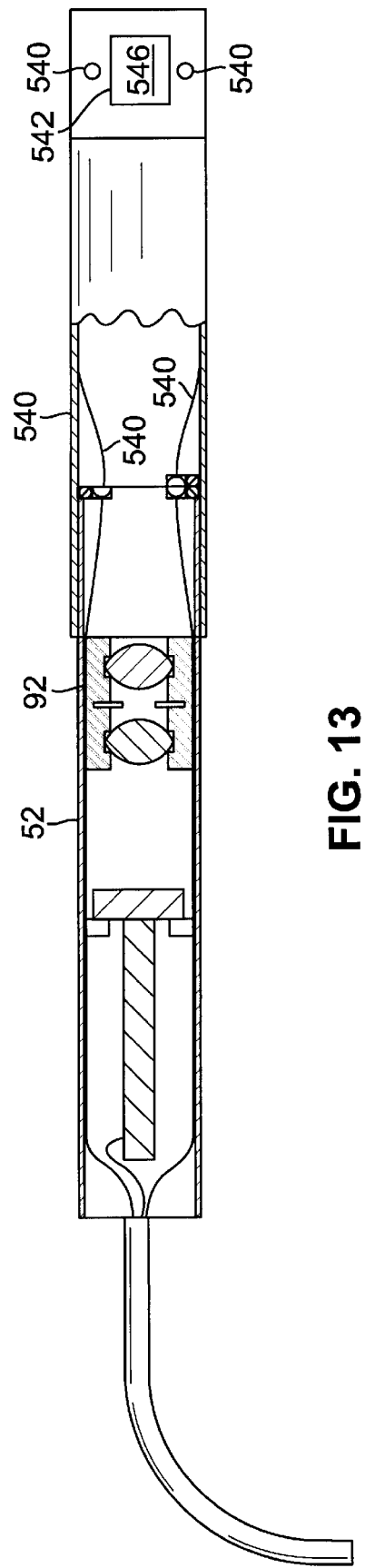
FIG. 13 is a side view of another embodiment of the handpiece, for intra-oral recording of at least a portion of the mouth.

Preferably, the system of the present invention can also be used to illuminate and record part or all of a patient's mouth. Such images are often used for patient instruction and orientation. The handpiece 50 of FIG. 2 can be adapted for such intra-oral recording by use of a different mouthpiece. An appropriate mouthpiece 540 is shown in FIG. 13, connected to the handle 52. The mouthpiece 540 includes two optical fibers 542, 544, whose outputs are at the front end of the mouthpiece, to illuminate the mouth. A window 546 receives the light reflected from the teeth. A mirror behind the window 546, angled 45° with respect to the surface of the window, reflects the light towards the lens assembly 92, which focuses the light onto the CCD 88, as described with respect to FIG. 2. The handle 52 of the handpiece 540 is the same as described above.

Alternatively, a separate camera and handpiece could be used. A separate camera could be preferable because a different type of camera may be found to be more suited for each procedure. For example, a black and white camera may be found preferable for imaging a tooth while a color camera may be found preferable for intra-oral recording. A suitable color intra-oral camera is a Vistacom from Air Techniques, Inc., Hicksville, N.Y., for example.

Returning to the system of FIG. 1, the CCD camera 24 produces a digitized electronic image which is transferred to the computer 26, which causes a digital image to be displayed on the monitor 28, providing visual feedback in real time to the operator.

The foot control 34 is preferably provided to enable the operator to control such actions as capturing an image for storage to disk without having to release his or her hands from the handle 22 or from the patient's mouth. Such a function could be provided through the hand control 36 coupled to the handle 22, as well.

The quality of the displayed image may be judged subjectively by the operator for its perceived utility for diagnosis and the image can be adjusted, if necessary. The operator can adjust the intensity and wavelength of the illumination, and other imaging parameters such as exposure time, through the keyboard 30, the mouse 32 or the hand control 36, until the image quality is satisfactory. The computer 26 can also automatically control certain imaging parameters, such as the intensity of the light, as discussed further, below.

Preferably, the operator may also select a region of interest ("ROI") in the displayed image by dragging the mouse 32, for example. The operator can also select the level of digital magnification of the ROI through the keyboard 30 or the mouse 32.

Preferably, the operator may also override the computer control of the imaging process, such as the computer's control of the intensity of the light. The override can be provided on the hand control 36 and/or the foot control 34, for example.

Image display on the monitor 28 or by the optional printer 38, facilitate comparison with other imaging modalities, if desired. Examples of such modalities include digitized dental x-ray films, digital radiographs, reflection-photographic images from an intraoral camera, or previously taken images.

Figure 14:
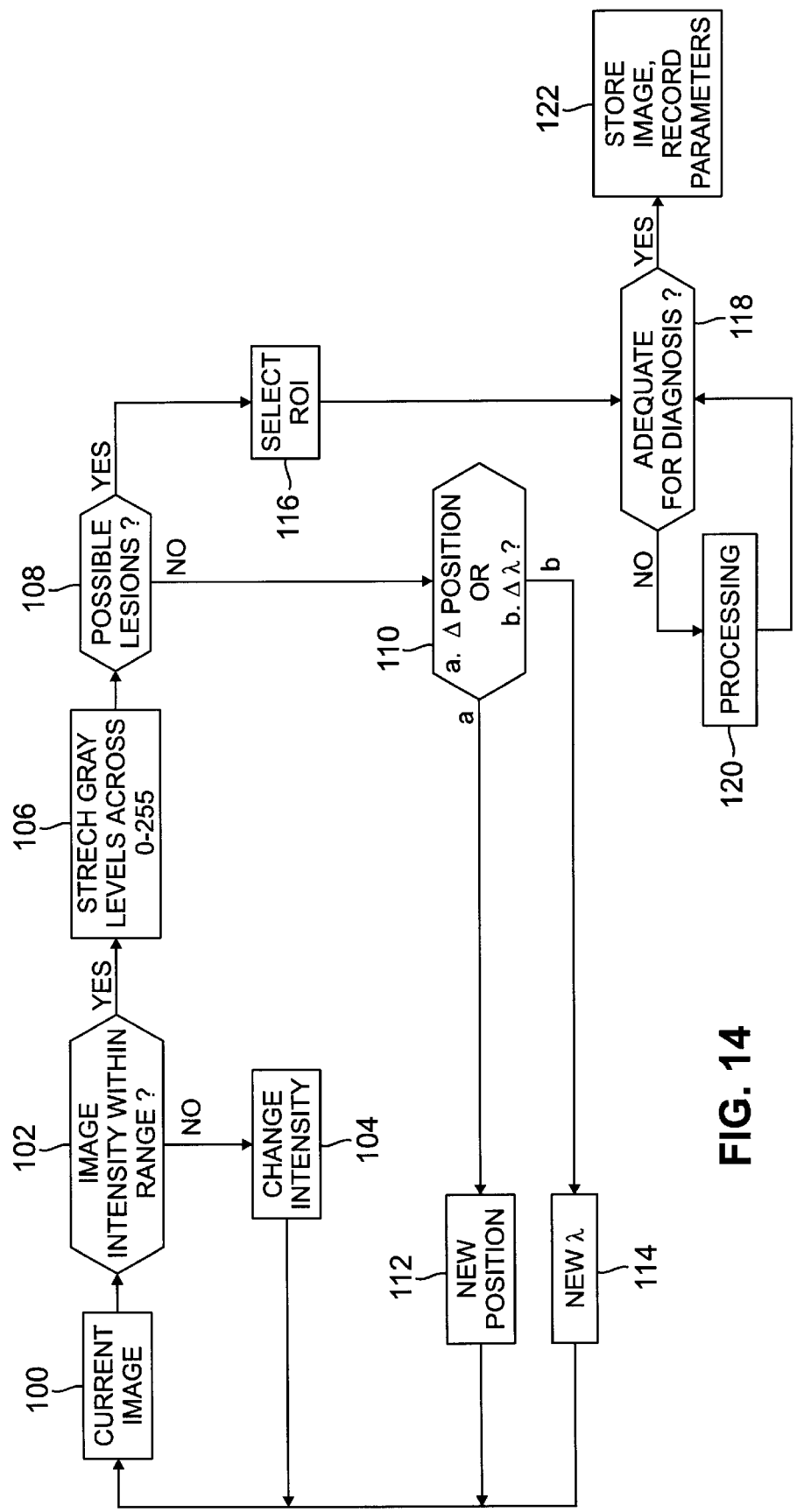
FIG. 14 is a flow chart of a method of controlling image acquisition parameters according to one embodiment of the present invention.

FIG. 14 is a flow chart of a method of controlling the acquisition and processing of images in accordance with the preferred embodiment of the present invention, wherein the operator has the ability to observe processed images in near real time. An operator can capture a desired image of a tooth under examination at step 100. The electronic representation of the captured image of the tooth is referred to as the "current image." The image is analyzed by the computer software at step 102 to determine whether the maximum image intensity is within a predetermined range. The upper limit of the range is defined by the saturation level of the pixels of the image. The lower limit of the range is a predetermined threshold value. Saturated pixels, which would show up as fully white on the monitor 28, do not provide the contrast resolution necessary for caries detection. The saturation level corresponds to a gray level of 255 in the 8-bit representation. A practical lower limit of the range is about 240. If there are any pixels at the saturation level, the appropriate control is adjusted by the computer 26 to reduce the intensity of the illuminator source 11 at step 104. Similarly, if the maximum gray level in the current image is below the lower limit, the intensity control is adjusted by the computer 26 to increase the intensity of the illuminator source 11 until the maximum gray level in the image exceeds the lower limit. If the CCD photodetector saturation level is 1023 in a 10-bit representation, the corresponding range would be greater than about 950 and less than about 1023. Steps 100–104 are repeated until the maximum gray level in the image is less than 255 and greater than 240 in an 8-bit representation.

Overall image brightness may also be adjusted by the operator based on his observation of the image on the monitor. The operator can override the intensity set by the software, if desired.

When the maximum image intensity at each CCD photodetector is within the desired range, or this requirement is overridden, a linear map of the gray levels in the image to a fixed, standard range desired for subsequent image processing is provided in step 106. For the 8-bit example of FIG. 14, the linear map of gray levels will typically correspond to a "stretch" of the initial intensities spanning the range of from 10, for example, to between about 240 to 255, into gray levels that span a standard range, 0–255 in the preferred embodiment. The standard range of 0–255 is applicable, even if the raw data from the CCD photodetector 88 are represented by a greater number of bits, such as 10 bits, because currently, almost all image processing software only employs the most significant 8 bits of the signal. While specifically discussed with application to a CCD 18 in the preferred embodiment, feedback control of intensity would be useful with any electronic camera, whether the images are digitized or not, and such intensity control is a feature of the present invention.

Once the image intensities have been stretched or mapped to the standard range at step 106, the operator examines the image displayed on the monitor 28 for local variations in image brightness that are atypical of normal teeth and that represent a possible lesion, in step 108. If no such atypical regions are found, the operator can decide whether to change the position of image acquisition or change the wavelength of illumination at step 110. At step 112, the image acquisition position with respect to the tooth can be changed by rotating the handpiece 12 about the pivot pin 62 from the intermediate position to either of the stop surfaces 84, 86, or any position between the stop surfaces, by slightly moving the handpiece 12 coaxially about the tooth 18 under examination at step 12. See FIGS. 7a, 8a, 9a. The handpiece 12 can be moved over another tooth at step 112, as well. The wavelength can be changed by advancing the filter wheel, for example, through either the mouse 32, the keyboard 30, hand control 36 or foot control 34, at step 114. The new image becomes the "current image" of step 100 and is evaluated at steps 102–104, as described above. Steps 108–114 are repeated until the image display contains a region of inhomogeneity that is suggestive of a possible lesion.

When the operator identifies a possible lesion, the operator selects a ROI over the relevant portion of the current image in step 116, and then determines whether the image of the selected region is adequate for diagnosis, in step 118.

If the image of the ROI is inadequate, the ROI is preferably analyzed by image processing software, in step 120, to improve its suitability for diagnosis. The image processing is described in more detail, below. Based on the information provided by the processed image displayed on the monitor 28, the operator decides whether the clinical information available in the ROI is adequate for diagnosis, at step 118. If the operator signals via the keyboard 30 or mouse 32, or the other modes of control discussed above, that the image is adequate, the image is stored, along with ancillary data, in the storage medium associated with the computer 26, in step 122. Ancillary data include control parameters associated with the image, which is preferably automatically entered by the computer 26, and any recorded annotations such as the dentist's diagnosis, the date of the procedure, or name of the patient, which the operator may enter at the keyboard 30. Hard copies of images selected by the user may be optionally output, either immediately or at a convenient later time, by the printer 38.

The digital image processing conducted at step 120 provides visually enhanced representations of variations in the image that help the dentist diagnose the condition of the tooth. Preferably, several options are available. For example, digital zooms into and out of the ROI, wavelet amplitude and phase-representations, iso-intensity contours and line scan profiles, may be provided and selected. Digital zooms into the ROI magnify the image. Digital zooms out of the ROI enable the operator to view the area surrounding the ROI, as well as enabling selection of a different ROI. Iso-intensity contours may assist in identifying local gradients which are characteristic of caries. Different intensity levels can be represented by different colors to further enhance the image visualization. Line scan profiles may also be provided, which can serve to indicate certain asymmetries characteristic of the presence of caries.

Multiresolution wavelet amplitude representations of the gray-level images provide the operator with bandpass-filtered visualizations that serve to enhance edge contrasts. "Chains" of wavelet amplitude maxima are preferably used to provide image segmentation. Displays of wavelet phase representations are preferably provided to help visualize tooth surface and texture information. For example, rugate structures in the region of dental enamel tend to correspond to pitted surfaces. Wavelet amplitude and phase representations provide contrast enhancement and quantitative measures of differences between sound and carious tissues are preferably provided as well. Wavelet signal analysis is discussed further, below.

In addition to providing graphic displays that aid in visualization, the preferred embodiment of the present invention permits the operator to display on the monitor 28 one or more computer-calculated numerical measures of selected properties of the image which can assist the dentist in interpretation. Examples of such measures are average and peak values over the region of interest of the image contrast and its spatial gradient.

It may be advantageous to compare current images of a tooth with previously taken images to monitor changes in the structure of the tooth over time. Image pattern matching software techniques are also, therefore, preferably provided for analyzing the images both in the gray-level, spatial domain and in the wavelet coefficient domain, to assist in monitoring such changes, which is also discussed further, below.

To demonstrate the feasibility of the present invention, a laboratory version of a digitally imaged fiber-optic transillumination system ("DIFOTI™") was prepared to obtain and study digitally acquired transillumination images of teeth in vitro. FIG. 15a is a schematic representation of the laboratory apparatus 500. Images obtained with this apparatus are referred to as "DIFOTI™ images".

Illumination was provided by a low-voltage 21-Watt metal-halide, short-arc lamp 502 whose intensity was controlled by an adjustable, stabilized power supply 504. Illumination optics (not shown) provided a collimated region for insertion of interference filters 506 which defined the spectral band. Six filters were used between 450 and 700 nm, in steps of 50 nm. The lamp 502 was coupled to a flexible light guide 508 for delivery of illumination to the target tooth 510. Two light guides of different fiber sizes were used: a 0.22 NA single fiber (0.365 mm aperture) and a multi-fiber bundle (3 mm aperture). Both guides provided sufficient illumination to acquire transillumination images with the narrow-band interference filters in place. The fibers were fitted with nonreflecting shrouds, and mounted on a machinist's height gauge for positioning in all three directions (x,y,z) and for determining the angle between the imaging direction and the normal to the tooth. The specimen teeth were attached with plasticine to a precision rotation table 512, which was mounted on a translation stage fastened to a lab jack, permitting angular and translational positioning of the specimen tooth. An imaging camera 514 was positioned on the side of the tooth 510 opposite the light guide 508. The imaging camera 514 was connected to an i486 PC computer 516, which processed and stored the images. Image analysis was implemented by software routines written in C++ programming language, such as those discussed below. A video monitor 518 was connected to the computer 516.

The imaging camera 514 was a Toshiba ½"570× high-resolution CCD (720×570 pixels), equipped with a 23-mm Schneider $f/1.4$ Xenoplan lens and an extender for reducing the field-of-view (FOV). The aperture and focus were adjustable. The image calibration scale was 43 pixels/mm over a 11.5-mm FOV.

The relative efficacy of DIFOTI™ and radiological imaging for the diagnosis of caries was compared by analyzing 50 teeth which had been set in modeling stone and preserved in 10% buffered formalin. The teeth included 15 incisors, 8 canines, 12 premolars and 14 molars, with and without caries. Each tooth was subjected to visual inspection under 4× magnification, explorer and, where warranted, histological section, by two experts, to determine whether caries was present in each tooth. The consensus of these experts served as the standard for the evaluations of DIFOTI™ and radiological performance.

Six DIFOTI™ images of each of the 50 teeth were obtained with six different controlled, repeatable camera/illuminator viewing geometries, with the system described, above. Three angles of incidence were used, each with facial and lingual illumination. FIGS. 16a–16f are examples of such images taken with the apparatus of FIG. 15. FIGS. 16a–16c are lingual views and FIGS. 16d–16f are labial views, respectively, of the same tooth at different angles of illumination and directions of view. The illumination was coaxial with the direction of view, as indicated in each figure by the inset.

An additional image was acquired of the transilluminated occlusal surface of each premolar and molar. Clinically interesting features, such as existing restorations, recurrent lesions, or cracks near the tooth surfaces are "seen" from the side that faces the camera, but not from the opposite side, as shown in the facial and lingual views of FIGS. 16a–16f.

Conventional radiographs of the same 50 teeth were produced using GENDEX™ x-ray equipment, at 70 KVp, 7 ma, at 15 impulses, and recorded on Ektaspeed Plus™ film. The geometry was the same as that used in clinical practice in vivo.

Five dentists experienced with oral diagnosis were used as readers of the radiological film images. Four of these dentists were also trained to read DIFOTI™ images in a two-hour session on the principles of the method.

The dentists were asked to determine the presence or absence of caries and the location of the caries relative to the tooth surfaces. The diagnosis based on the DIFOTI™ images and the x-ray images were compared to the diagnosis of the experts. The sensitivity, or ability to correctly identify carious tissue, and the specificity, or ability to correctly identify healthy tissue, were evaluated.

The sensitivity of DIFOTI™ was found to be superior to that of x-ray. The sensitivity was twice as high in identifying approximal caries, three times as high in identifying occlusal caries and ten times as high in identifying smooth surface caries. The specificity of DIFOTI™ was comparable to that of x-ray. Certain of the DIFOTI™ images indicated the presence of incipient and recurring caries while the corresponding x-ray images did not. Radiology, in contrast, has less lingual/facial differential.

The use of wavelet amplitude and phase representations for visual enhancement of individual images and in pattern matching between current images and previously taken images, will now be discussed. A two-dimensional wavelet can be seen as a collection of spatial filters in image processing or as a family of basis functions in mathematical representations. A rescaled prototype function performs the signal analysis at different resolution levels, such that in the wavelet transform domain, there is information about scale, position and frequency content. Wavelets are localized in both space and frequency. They have proven to be very useful in image compression and in applications where the images are statistically nonstationary. Wavelet representation is discussed in S. Mallat, S. Zhong, "Characterization of signals from multiscale edges," IEEE Transactions on Pattern Analysis and Machine Intelligence", Vol. 7, No. 7, pp. 710–732, July, 1992; and S. Mallat, S. Zhong, "Singularity detection and processing with wavelets", IEEE Transactions on Information Theory, Vol. 38, No. 2, pp. 617–643, March 1992, for example.

Many different wavelet representations of images are available. A wavelet maxima representation method which can be used both for image compression and for feature analysis and extraction, is preferred. Mallat's wavelets for image compression, which have been very successful in detecting boundaries between tissues with different x-ray transmissions, are particularly preferred. See, for example, Mallat, S., "A theory for multiresolution signal decomposition: The wavelet representation, IEEE Transactions on Pattern Recognition and Machine Intelligence, Vol. 11, No. 7, pp. 674–693 June 1989, which is incorporated by reference herein. Wavelet representations have not been used in dental imaging applications such as DIFOTI™, where the presence and location of inhomogeneities in the image due to changes in tooth structure must be determined in the presence of multiple scattering of the transmitted light.

The multiresolution wavelet representation provides a hierarchical framework for the interpretation of image information. At different resolutions, the details of the image generally characterize different physical structures of the scene. Different objects in a scene have signatures in the wavelet representation which differ from each other and from noise. Since the edges of an object propagate across scales in a specific manner, the shape can be extracted from its wavelet representation.

The sequence of resolution parameters $r_j = 2^j$, varies exponentially with index j on a dyadic scale over a finite range. The details at each resolution are calculated by filtering the original image with the difference of two low-pass filters, or with a bandpass filter which is generated by the wavelet prototype. At scale ("level") j=1, the wavelet uses information weighted over 2 pixels in each direction. The filter is scaled by a factor of two at level j=2, which considers information from 4 pixels in each direction.

In the wavelet maxima representation, at each scale $2^j$, the wavelet transform has two gradient-like components, $W_1 f$ $(2^j,x,y)$, $W_2 f(2^j,x,y)$. These components can be interpreted as the two coordinates of the gradient vector of the image smoothed with the scaling filter at scale $2^j$. The local maxima of the modulus of this filtered gradient correspond to the edges of the image at the scale $2^j$.

The preferred method of tooth image segmentation is based on looking for the "longest" chain among the chained maxima at each level in the wavelet domain. Since there generally is an edge discontinuity at the enamel border of a directly illuminated tooth, past which little light is transmitted to neighboring teeth, the boundary of the tooth under examination produces the longest chain. Consequently, the intensity at the boundaries of the neighboring teeth is almost never as high as at the boundary of the tooth being examined. It is noted that because the enamel is generally well illuminated, it is very unusual for the boundary defined by the longest chain to have branches. Since selecting the longest chain does not require either a global or a local threshold, the segmentation result is relatively invariant to the brightness of the illumination source.

Segmentation results at different levels are not expected to be identical, because resolution degradation occurs in computing at higher levels of the wavelet representation corresponding to coarser scales. Nevertheless, such differences do not affect the repeatability of segmentation, as long as the segmentation is always done at the same level.

In the preferred method of wavelet representation, the DIFOTI™ image is first subjected to a fast dyadic discrete wavelet transformation in the redundant discrete wavelet representation ("RDWT"). RDWT as used herein is defined below:

$$\text{RDWT}_m(x',y') = m^{-1} <f(x,y), \Psi(m^{-1}(x-x'), m^{-1}(y-y'))> \qquad (1)$$

where $f(x,y)$ is the signal to be transformed, and, in the redundant basis, the shifts x' and y' are non-negative integers, and where it is preferred that the basis representation be separable, $\Psi(x,y) = \psi(x)\psi(y)$, wherein $\psi(x)$ and $\psi(y)$ are bandpass filters that need not be identical, and that are orthogonal to each other, i.e., biorthogonal. It is noted, however, that $\Psi(x,y)$ could be any wavelet filter function that has finite energy ($L^2$ norm) and that has translations and dilations orthogonal to each other. Equation 1 is an extension in two dimensions of the one dimensional example of Aldroubi, Akram, et al., Wavelets in Medicine and Biology, CRC Press, Inc. (1996), pp. 17–18.

In contrast, in the conventional, nonredundant discrete wavelet transformation, downsampling to remove redundancy is done by choosing translation steps to be multiples of 2, to separate information into different levels. Thus, in the nonredundant wavelet basis, $^k\Psi_m(t)$, where one chooses $m = k2^j$ for integer $k,j \geq 0$. Although the conventional method removes unnecessary information at each level, the horizontal and vertical dimensions of the image at successive levels are half those at the previous level. This is inconvenient when image segmentation is to be performed, however, since it is desirable to maintain the original spatial positions. Therefore, the redundant wavelet transform is preferred.

The "low-high" and "high-low" gradient-like components of the representation are then selected. The "low-high" component acts as a low pass filter of the x coordinate and a high pass filter of the y coordinate. Similarly, the "high-low" component acts as a high pass filter of the x coordinate and a low pass filter of the y coordinate. In the two-dimensional generalization of the redundant representation, the transformed position is denoted by (x',y') and the shorthand "high-low" and "low-high" notation below, is employed:

$$RDWT_{HL}(x',y')=2^{-1}<I(x',y'), \Psi_{HL}(2^{-1}(x-x'), 2^{-1}(y-y'))>,$$

$$RDWT_{LH}(x',y')=2^{-1}<I(x',y'), \Psi_{LH}(2^{-1}(x-x'), 2^{-1}(y-y'))>, \quad (2)$$

where the transformation basis functions are:

$$\Psi_{HL}{}^m(x',y')=\bar{\psi}_m(x)\phi_m(y)$$

$$\Psi_{HL}{}^m(x',y')=\phi_m(x)\bar{\psi}_m(y)$$

$\phi_m(x)$ and $\phi_m(y)$ are biorthogonal bi-splines and $\psi_m(x)$ and $\psi_m(y)$ are their respective spatial derivatives.

The direction of $\theta(x',y')$ spans the range $-\pi \leq \theta \leq \pi$, and is defined by the two-argument arctangent function:

$$\theta(x',y')=\arctan(RDWT_{HL}(x',y')/RDWT_{LH}(x',y')) \quad (3)$$

The measure of coefficient magnitude is the root-sum-square of the "low-high" and "high-low" components:

$$magnitude(x',y')=sqrt(RDWT_{HL}(x',y')^2+RDWT_{LH}(x',y')^2), \quad (4)$$

The computed directions are then discretized to one of the eight values indicated on the matrix in FIG. 17a, wherein the numbers 0 through 7 correspond to the $\theta$ directions shown in the diagram in FIG. 17b.

Figure 18:
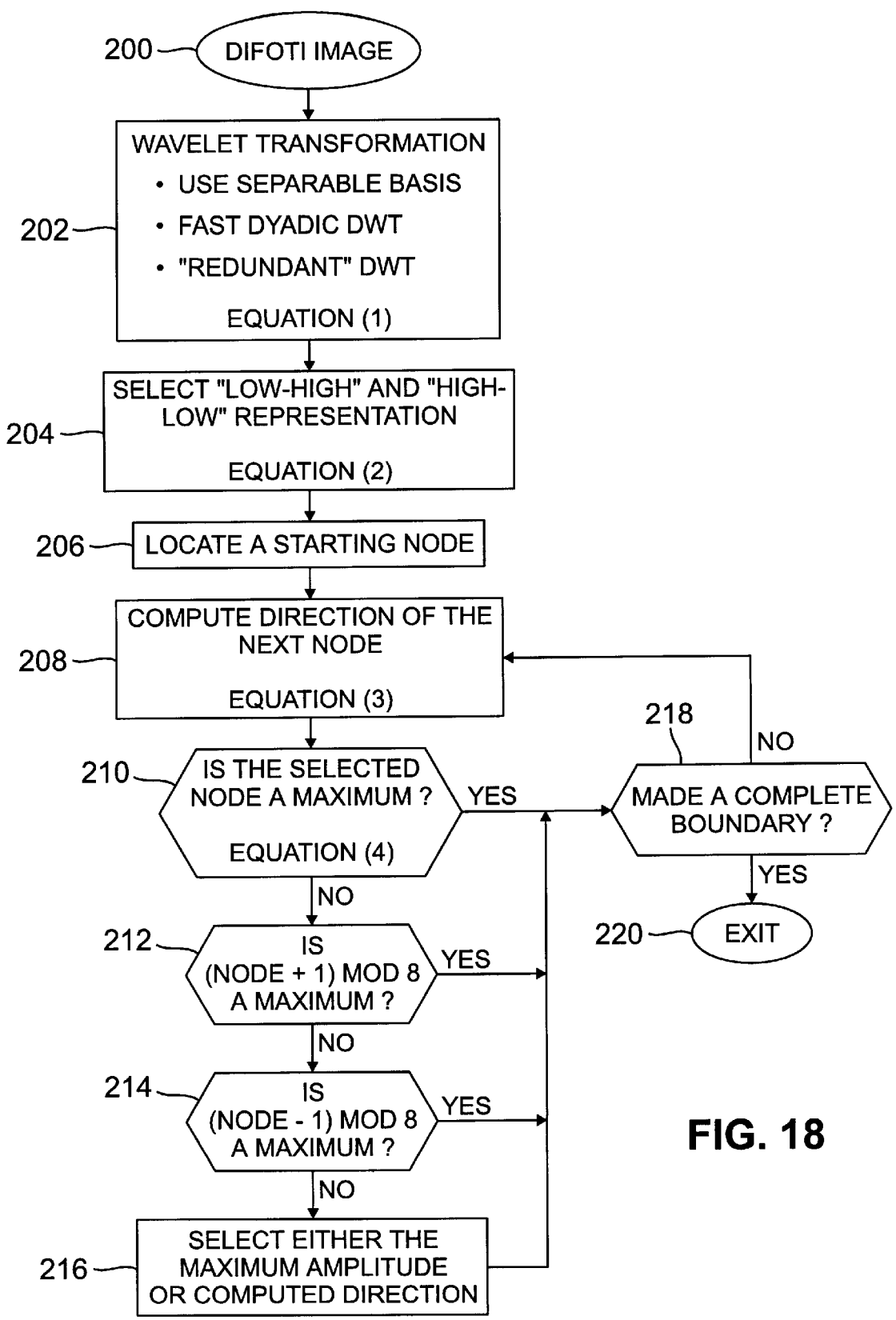
FIG. 18 is a flow chart of a preferred wavelet segmentation procedure used in the present invention.

FIG. 18 is a flow chart of a preferred procedure. The DIFOTI image 200 is subjected to the fast dyadic discrete wavelet transformation in the redundant discrete wavelet representation in accordance with Equation 1.

Next, the "low-high" and "high-low" components are selected, by Equation 2, in step 204.

A starting node for the segmentation boundary is located in step 206. This may be done by the operator, who can choose any point on the display that clearly lies on the desired boundary. Alternatively, a default position on the tooth boundary is selected by the algorithm by proceeding from the intra-oral background towards the tooth boundary at its occlusal or incisal surface.

Then the direction of the next node for the segmentation curve is selected using Equation 3, in step 208.

It is then determined whether the coefficient magnitude at the selected node is a maximum using Equation 4, in step 210. The maximum magnitude is defined as the largest magnitude over the matrix in FIG. 17a.

If the selected node at step 210 is not the maximum, it is determined whether the next node ((node+1) mod 8), is the maximum at step 214. If not, then it is determined whether the prior node ((node−1) mod 8) is the maximum in step 212. Because directions are chosen from the discrete set of eight, numbered 0 through 7 in FIG. 17a, the selections of the next node are denoted as "modulo 8" in the flow chart. As the program advances to each node, the operator can observe the generation of the boundary curve on the image, and override the computed boundary, if necessary.

If neither the selected node, the next node, nor the prior node is a maximum, then the program will either select the next node on the curve ((node+1) mod 8) to be a maximum-amplitude point, or will select a point lying along the computed direction of the boundary curve to be a maximum, where the maximum amplitude and computed direction are determined via Equations 3 and 4, above, in step 216. Which procedure the program will follow may be determined by the operator prior to the session.

If any of the nodes checked in steps 210–214 are the maximum, or the maximum amplitude or computed direction is chosen at step 216, it is then determined whether the boundary is complete in step 218. The boundary is complete when the generated curve returns to its starting point or node. If the boundary is complete, the routine is exited at step 220. If it is not, then the routine returns to step 208, and steps 208–216 are repeated.

The method of segmentation represented in FIG. 18 has been implemented in software written in the C++ programming language, and executed on an IBM-compatible PC for transillumination images obtained with the laboratory apparatus of FIG. 15. The applicable routines implementing the procedures of FIG. 18 follow this description of the invention.

Figure 19A:
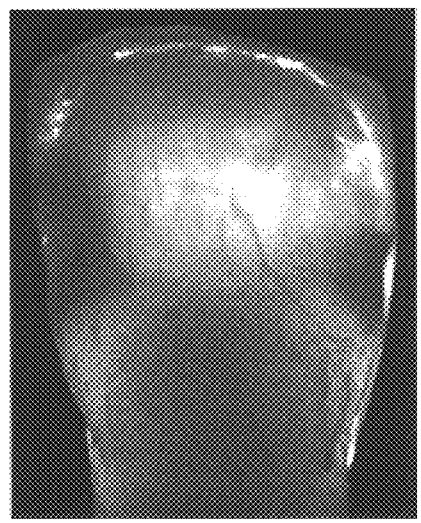
FIGS. 19a–19c are a series of images showing an unprocessed image, and corresponding wavelet amplitude and wavelet phase representations of the unprocessed image, respectively, at different levels of wavelet transformation.
Figure 19B:
Figure 19D:
Figure 19C:
Figure 19E:

FIG. 19a is an unprocessed image obtained white light. FIGS. 19b and 19c are different levels of wavelet amplitude representations and wavelet phase representations, respectively, of FIG. 19a. The top image is at level 1 and the bottom image is at level 3. The borders associated with rapid changes in the local image intensity are clearly evident in the amplitude representations of FIG. 19b. Near the tooth surface, these representations tend to correlate with the borders between carious and normal tissue. The directions of local gradients are manifest in the phase representation, where the presence of frank caries (indicated by darker regions in the unprocessed images that correlate with the presence of frank caries) give the appearance of deep craters, which may be useful for clinical visualization, as shown in FIG. 19c. Different levels of clinical detail can be extracted from wavelet components of different spatial resolutions. An example of the texture of the tooth surface facing the camera can be visualized in the phase representation of FIG. 19c, which indicates a rugate structure, corresponding to a pitted enamel surface.

Figure 20A:
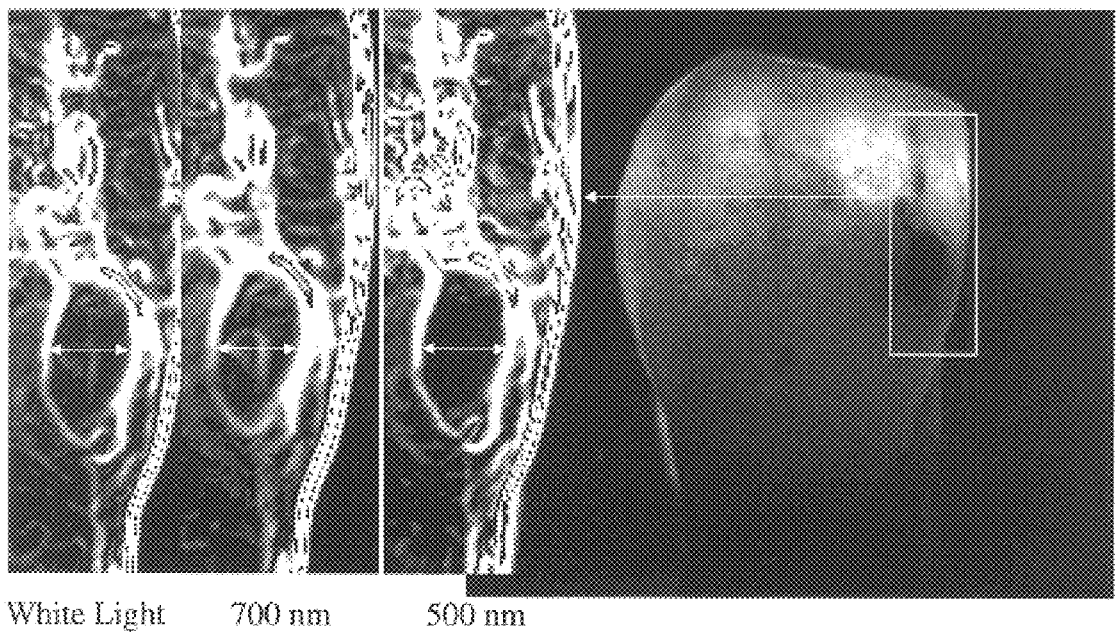
FIG. 20a is a series of images showing the effect of changes in wavelength on the images resulting from the wavelet representation.

FIG. 20a shows the effect of changes in wavelength on the images resulting from wavelet representation. The right-hand portion of FIG. 20a shows a raw DIFOTI™ image obtained at 500 nm. The left-hand images are in wavelet magnitude representation and were obtained at 500 nm, 700 nm, and in white light, as indicated. The contours between carious and noncarious tissue are clear. In this representation, the area of the lesion is uniformly dark at 500 nm.

In the image at 700 nm and in white light, fine structure appears inside the lesion area. In all three panels, the wavelet representation in the sound tissue surrounding the caries indicates nonuniform intensity associated with light viewed through nonuniform anatomical structures. The wavelet representation illustrates that the 500 nm illumination was absorbed uniformly by the frank caries, whereas some of the 700 nn (and white-light) illumination was nonuniformly attenuated by the caries lesion.

Figure 20B:
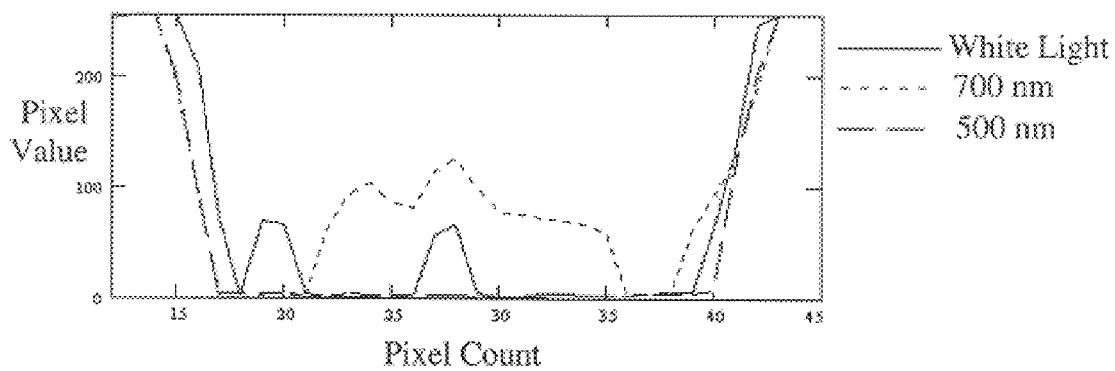

FIG. 20b is a graph of line scans across the lesion at the positions indicated by thin white lines in the three left panels in FIG. 20a. These line scans represent the wavelet amplitude variation profiles across the lesion image, for white light, and for narrow-band illumination at 700 nm and 500 nm, as indicated. The amplitudes in the 500 nm image are negligibly small in the lesion area (pixels 17 through 38), and there is greater variability inside the lesion at 700 nm than with white light. The highest contrast is provided at 500 nm.

In the preferred embodiment of the invention, current images of a tooth are compared to earlier images of the same tooth, to monitor for detrimental or ameliorative changes over time. To achieve robust pattern matching for measuring changes in tooth tissue structure, one requires a representation which is insensitive to overall light intensity variation but is able to enhance structural changes in segmented teeth. This is achieved in the preferred embodiment by the wavelet maxima representation, which can compare images with intensity differences of up to about 25%. If the intensity is adjusted to a value which varies by more than about 25% from the intensity used in the prior image, the operator can override the intensity adjustment and set a desired intensity in the region of interest, as discussed above.

After segmentation of the tooth under examination, as discussed with respect to FIG. 18, above, position and orientation are computed from the gray-level images. The first moment of intensity, the centroid of the tooth under examination, is used to estimate the position of the tooth in the field of view. The orientation of the tooth is estimated from the second moment of intensity, the moment-of-least-inertia. See, for example, B. Klauss, P. Horn, "Robot Vision", Cambridge, Mass., MIT Press, 1986, pp. 48–53, p. 175. Since both these moment quantities are relatively insensitive to small local changes in the spatial domain, the representation, location and orientation of the tooth are estimated in the spatial domain, prior to pattern matching.

To actually provide the pattern matching between a current and a previously taken image of the same tooth, the dyadic wavelet transform was applied, and the wavelet coefficients for five resolution levels were stored. The coefficients were linearly expanded into full, 0–255 range. The dominant, source-intensity-sensitive signals were first dilated and filtered out. The gray level image of a tooth of interest in the spatial domain was segmented from the background using the longest modulus maxima chain at the finest level of wavelet representation, followed by an estimation of its location and orientation. The wavelet magnitude representation of each image at each level was also segmented by using the boundaries at that level to remove possible contribution from background such as a light tip, a gum or neighboring teeth. Each segmented wavelet magnitude representation of the "compared" image was then translated and rotated with respect to the "original" image.

Figure 21:
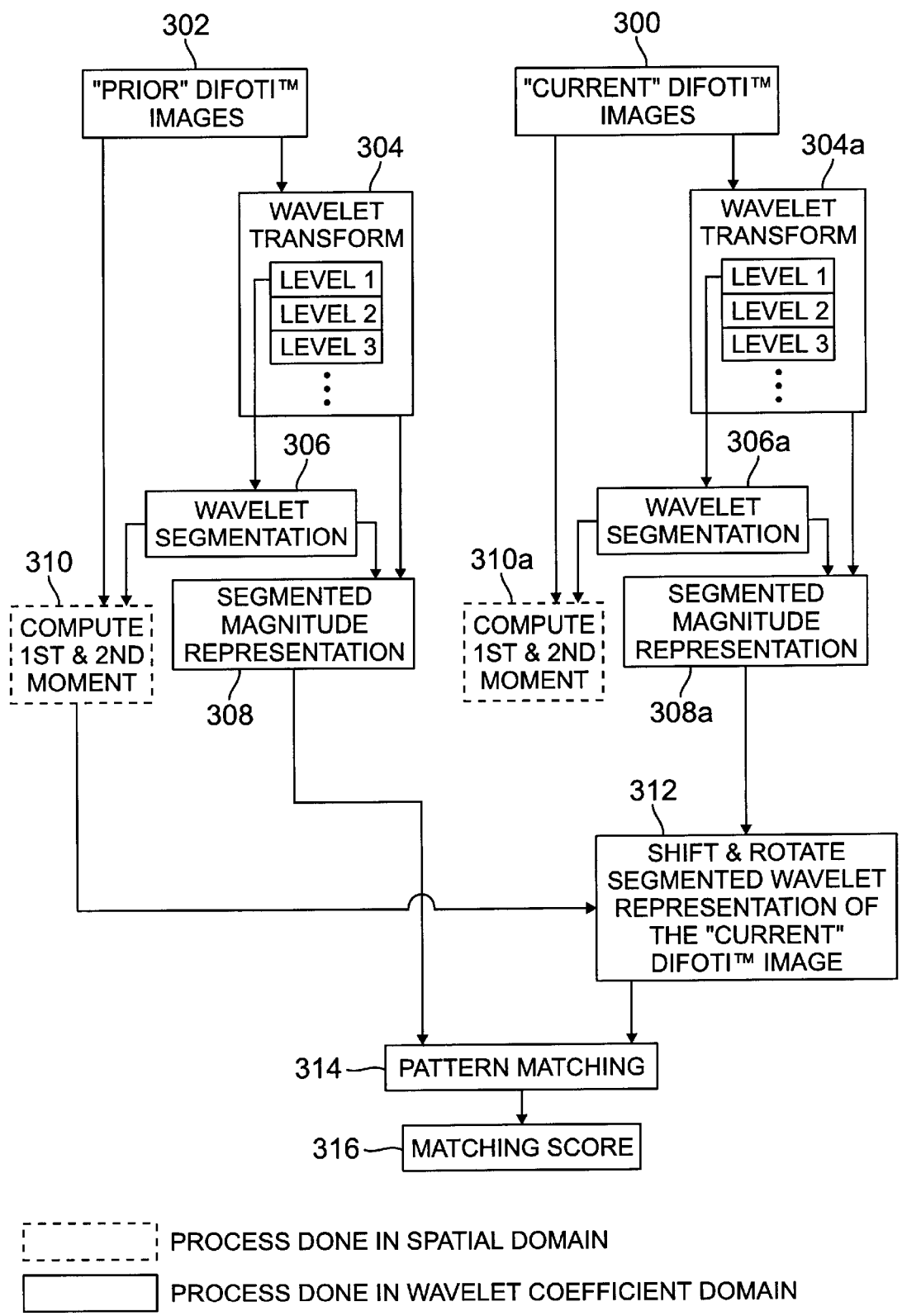
FIG. 21 is a flow chart of a preferred pattern matching procedure used in the present invention.

FIG. 21 is a flow chart of a preferred monitoring procedure employing images to monitor the changes in the tooth over time, such as changes in a mineralization front indicative of caries status. In FIG. 21, a current image including a particular tooth of interest is represented by box 300 and an image including the same tooth, obtained under similar conditions in a prior clinical session, is represented by box 302. Although both images are subjected to the same sequence of steps, as indicated by the parallel paths or data streams in the flow chart, since results of some or all intermediate steps in the processing sequence can be stored between clinical sessions, it is not necessary that the steps in these parallel paths take place simultaneously.

Some of the processing steps are performed directly on the gray levels of the recorded image. Such steps are indicated in FIG. 21 by dotted lines as occurring in the "spatial domain." Other processing steps, indicated by solid lines, take place in the wavelet coefficient domain. The combination of processing in both the wavelet and spatial domains has been found to provide more robust, accurate results.

The wavelet coefficient domain is entered for each image 300, 302 through the wavelet transformation at steps 304, 304a, which may correspond to step 202 in FIG. 18. Alternatively, other wavelet transformations, such as a non-redundant wavelet transformation, may be used. Non-redundant wavelet transformation may be preferred here because it encompasses fewer pixels, speeding computations. Steps 304, 304a indicate three or more levels. While Level 1 represents the scale that carries the finest detail in the image, it has been found that levels 2 or 3 provide better results, as discussed below. Coefficient magnitude representations of the wavelet-transformed images computed in steps 304, 304a are segmented in steps 306, 306a. Steps 306, 306a correspond to steps 204–220 of the flow chart of FIG. 18.

The image representations resulting from the wavelet segmentation steps 306, 306a include portions that correspond to adjacent teeth and gums and which are not needed for caries diagnosis. Therefore, the portions of the image outside the tooth of interest are preferably eliminated from the image in the spatial domain in steps 308, 308a, 310 and 310a. The same segmentation mask is applied to the image in the spatial domain in steps 310 and 310a and to its coefficient magnitude representation in steps 308, 308a. The latter are referred to as the segmented magnitude representations.

The first and second moments of the gray level distributions in each of the segmented images in the spatial domain are also computed in steps 310, 310a. The centroids of these distributions are located through the first moments and the principal axes of the inertia tensor are determined through the second moments, also in steps 310, 310a. The coordinates governing the relative position of the centroids in the two images are then adjusted to shift them into coincidence, in step 312.

One of the two images is then rotated with respect to the other to bring the principal axes of their gray level distributions into coincidence, also in step 312. In the example of FIG. 21, the current image 300 is shifted and rotated into coincidence with the prior image 302. It may be more advantageous to shift and/or rotate the prior image into coincidence with the current image, as is known in the art.

Once the two images have been segmented, shifted and rotated into corresponding representations of the same teeth, pattern matching techniques are employed in step 314. Normalized cross correlation ("NCC") performed on the segmented wavelet representations is the preferred method for pattern matching. NCC, and other correlation techniques are discussed in H. Hang, J. Woods, "Handbook of Visual Communications", New York, Academic Press, p. 157 ("Hang"), which is incorporated by reference, herein. NCC is defined as:

$$NCC(\bar{x}, \bar{y}) = \frac{\int\int_I I_1(x, y) \cdot I_2(x - \bar{x}, y - \bar{y}) dx dy}{\left(\int\int_I b_1(x, y) I_1^2(x, y)\right)^{1/2} \cdot \left(\int\int_I b_2(x, y) I_2^2(x, y)\right)^{1/2}}$$

where $(\bar{x}, \bar{y})$ represents a computed shifting factor (translation) of one image object relative to another, that is applied after rotation of the detected (and segmented) objects as described at step 312; and the indicator function $b(x,y)$ is "1" (one) when $I(x,y)$ belongs to the segmented object, "0" (zero) otherwise. This equation is slightly modified from that of Hang, to suit the present application. It has been found that NCC, whose numerator is linear in image differences, is less sensitive to roundoff errors in intermediate computer calculations than other techniques that require calculating the squares of such differences. Roundoff errors can be significant when the DIFOTI™ images of the same tooth, with at most slight differences, are being compared.

The result of this pattern matching process is a matching score in step 316, which is a numerical value whose deviation from a reference value such as 1.00 serves to indicate the degree of mismatch between the two patterns under comparison, derived in step 314. A value less than approximately 0.90 indicates sufficient change in the tooth to warrant further examination of the state of mineralization of the tooth.

A monitoring procedure similar to that of FIG. 21 was also implemented in software as described with respect to FIG. 18, using DIFOTI™ images obtained with the laboratory apparatus of FIG. 15. The applicable routines implementing the procedures of FIG. 21 also follow the description of the invention.

Figure 22A:
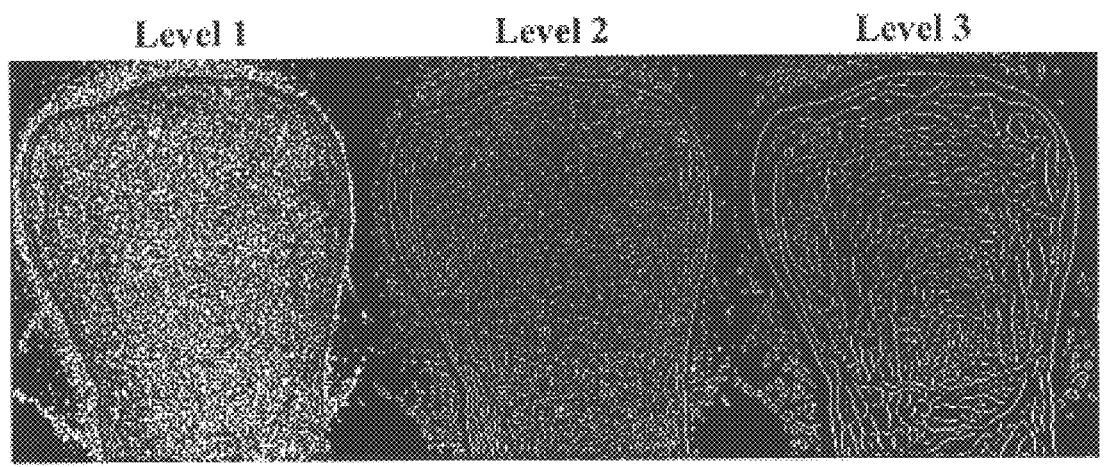
FIG. 22a are representations of modulus maxima in the wavelet magnitude representation of a tooth at levels 1–3 as indicated, for a DIFOTI™ image.
Figure 22B:
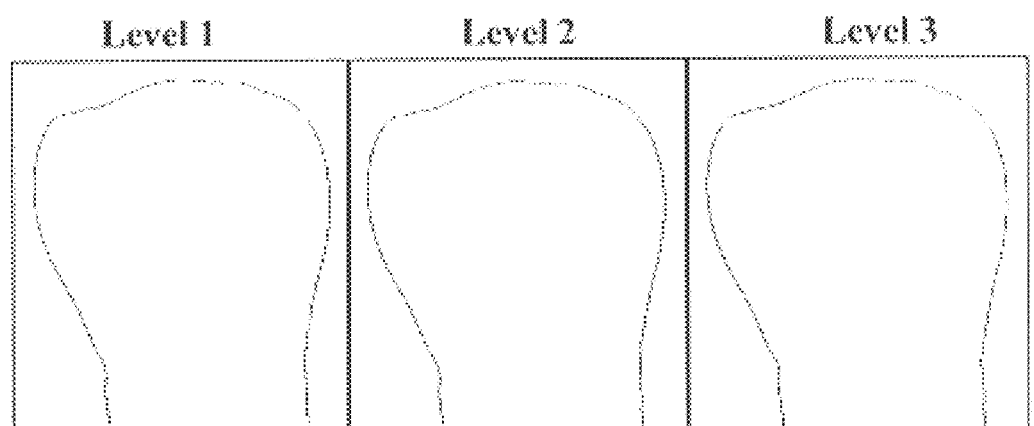
Figure 22C:
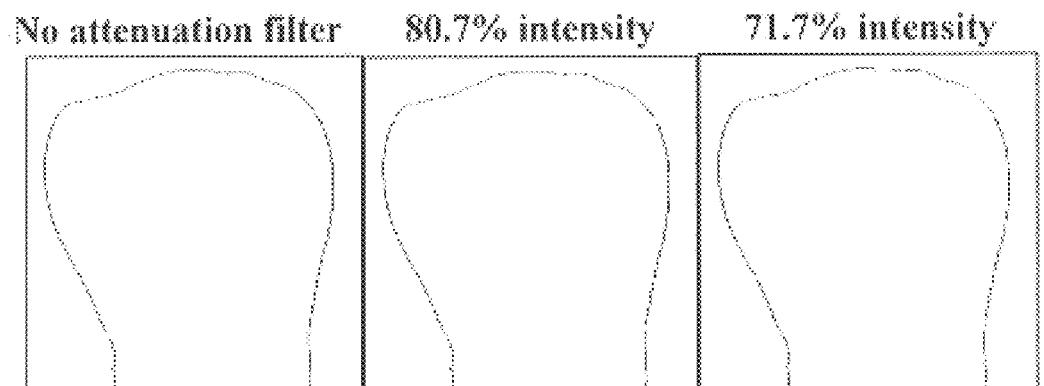
FIG. 22c shows the longest chain in the level 2 wavelet representation of the tooth in FIG. 22b, at various light intensities.

FIG. 22a shows a typical modulus maxima chaining representation in levels 1–3 for a DIFOTI™ image at 91.1% of initial intensity (nominally 9.1 mW). The supporting spatial-frequency ranges in both the x- and y- directions were: $n_0 \pm 23$ μm and $f_0 \pm 43$ mm$^{-1}$ at level 1; $n_0 \pm 46$ μm and $f_0 \pm 21$ mm$^{-1}$ at level 2; $n_0 \pm 92$ μm and $f_0 \pm 10$ mm$^{-1}$ at level 3; physical interpretation is based on the camera spatial resolution (43 pixels/mm). The results demonstrated successful segmentation of all teeth over the field of view, without exception. FIG. 22b shows the stability of the boundary resulting from the segmentation of the images of FIGS. 22a, using the longest chain in any one of these three levels of the wavelet representation. FIG. 22c shows the boundary resulting from the longest chain in the wavelet representations of the same tooth at various light intensities at level 2 wherein the image at the original intensity, nominally 9.1 mW, is compared with images for which the intensity is reduced to 80.7% and 71.9% of the nominal value. The segmentation results in the wavelet domain are repeatable within the range of illumination source intensity variations tested.

While wavelet segmentation of an image may depend on the level (resolution) used, segmentation at the same level is always repeatable, as illustrated in FIG. 22c. Repeatability of segmentation is an essential prerequisite to monitoring the status of a tooth over time.

Figure 23A:
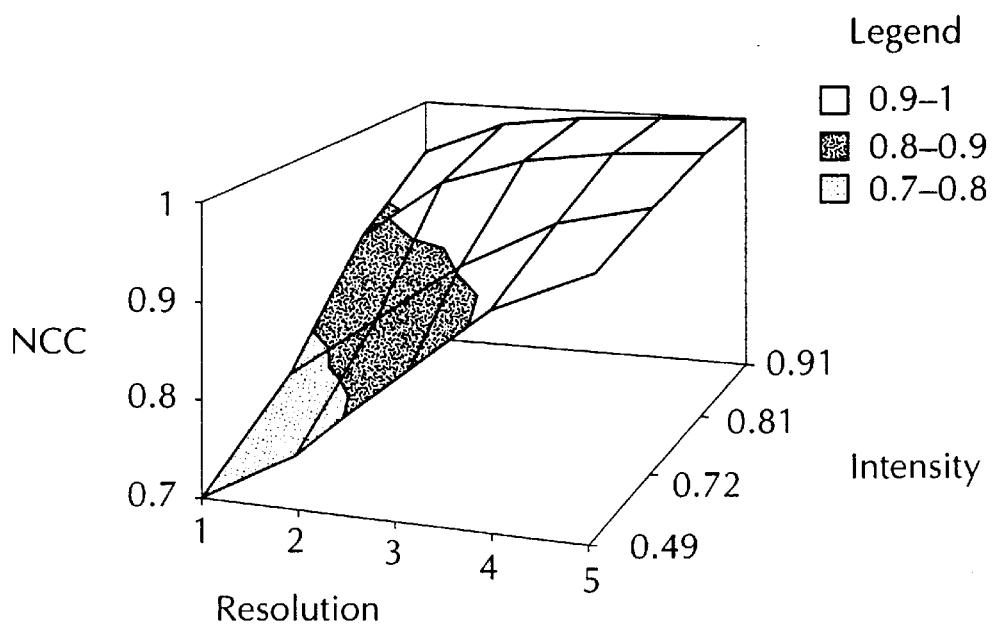
FIG. 23a is a 3-dimensional plot of NCC vs. wavelet resolution (Level) vs. relative light intensity (Intensity) for pattern matching in the wavelet domain in accordance with the procedure of FIG. 21.
Figure 23B:
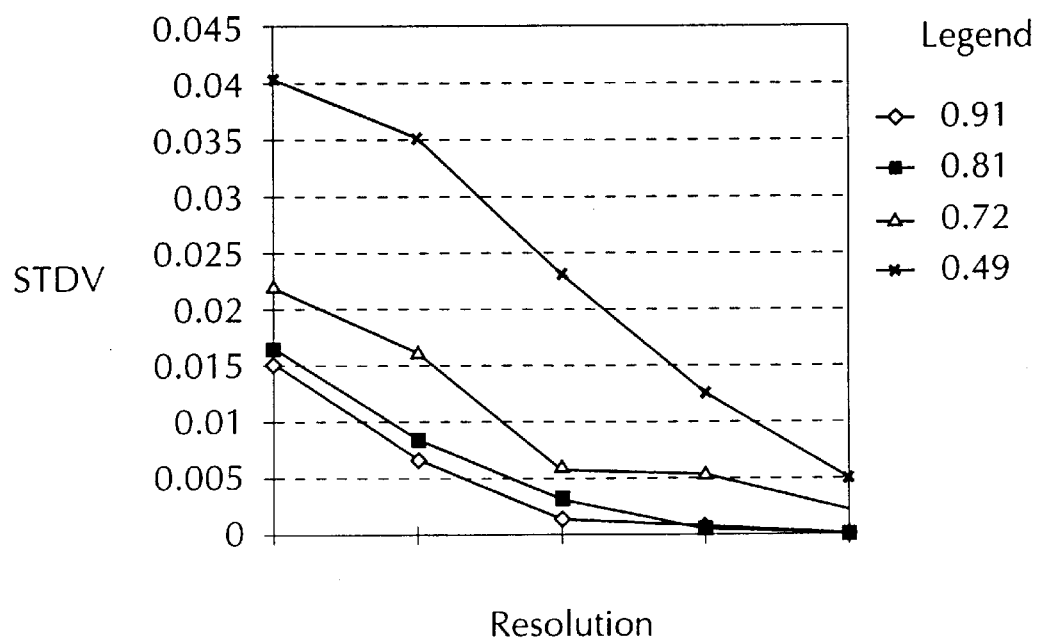

The results of pattern matching in the wavelet coefficient domain are summarized by the 3-dimensional plots of NCCs vs. wavelet resolution (Level) and vs. relative light intensity (Intensity) in FIG. 23a. Each point in the plot in FIG. 23a represents an average of the NCCs for 40 independent cases for images obtained with the laboratory apparatus of FIG. 15. FIG. 23b contains a plot of the standard deviation of the NCC values at the same grid points as in FIG. 23a. In FIG. 23a, for a reduction in intensity of up to about 30%, the NCC decreases by less than about 10%. The pattern matching method is therefore robust with respect to intensity changes. This robustness is independent of light wavelength or type of tooth.

While NCC is higher in the wavelet representation at coarser resolution, because the effects of noise are reduced by the low pass filter effect of the wavelet transformation, pattern matching is preferably performed at higher levels. For example, when the illumination source intensity is controlled to less than about 20%, the second level can be used. The standard deviations computed at this level, shown in FIG. 23b, are $\leq 1\%$. If the light source intensity is less well controlled, the pattern matching should be done at lower resolution, with the concomitant risk of insensitivity to small changes. The brightest region in FIG. 23a, representing NCCs over 90%, is within the preferred signal-to-noise trade-off range.

Figure 24A:
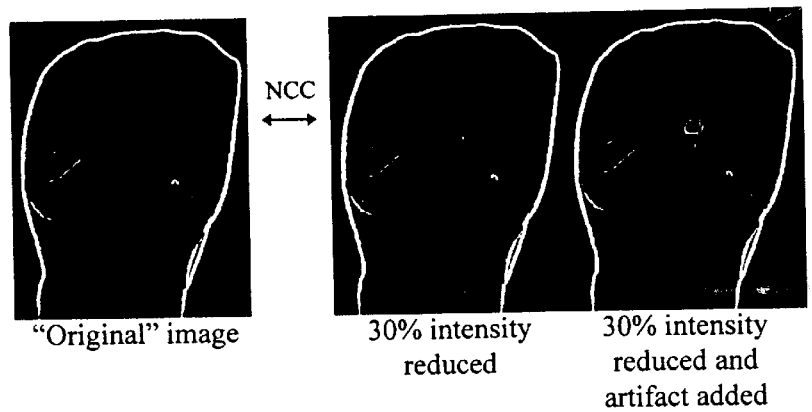
FIG. 24a is a series of images in wavelet magnitude representations, which were compared pairwise by computing the NCCs including an original image, an image with its intensity reduced by 30% and an image with its intensity reduced and with an artifact added.
Figure 24B:
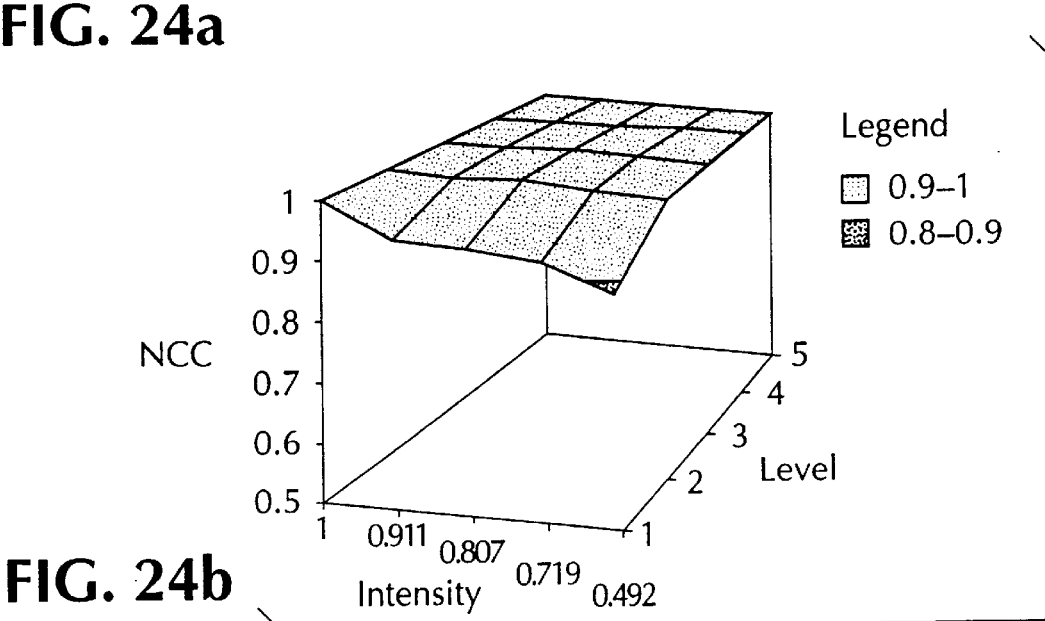
Figure 24C:
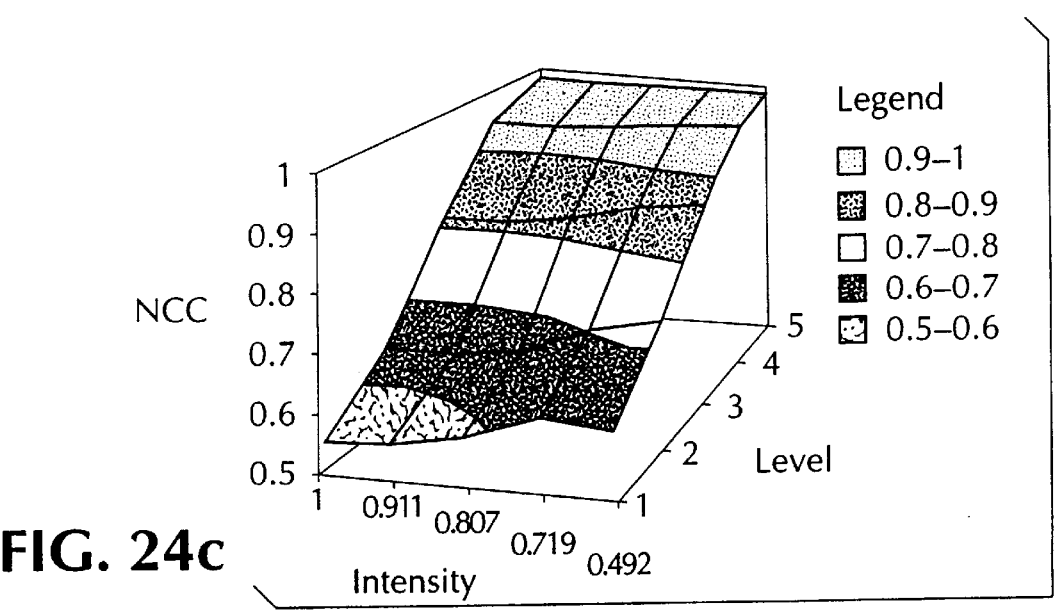
FIG. 24c is a 3-dimensional plot of NCC vs. intensity and resolution, showing the sensitivity to the simulated "lesion" structure of FIG. 24a in the wavelet coefficient domain.

Pattern matching ability in the wavelet-magnitude representation was tested by calculating the NCC between "original", images and "compared" images containing light absorption artifacts that simulated the presence of lesions. Wavelet representations at various levels show high sensitivity to changes occurring in the segmented lesion, relatively independent of illumination source intensity changes less than about 20%. An example of such wavelet-magnitude representation pairs is shown in FIG. 24a, in which the effect of the absorption artifact is clearly visible in the right-most image. The 3-dimensional plots of NCC vs. intensity and resolution in FIGS. 24b–24c show the desired sensitivity in the wavelet coefficient domain to the simulated "lesion" structure. Comparison of FIGS. 24b and 24c demonstrates that the wavelet coefficient domain provides sensitivity for measuring slight changes in tooth transmission, even when the light source intensity varies by up to about 20%. Similar robustness has been found with respect to small changes in control parameters such as viewing angle. The added "lesion" artifact causes the NCC matching score in FIG. 24c to drop by as much as 45%. The precise amount depends on the degree of variation in illumination intensity. This suggests that levels 4 and 5 may not be suitable for detecting small changes, because the NCCs at these levels remain above 90%. The results instead suggest that matching should be done at either level 2 or level 3, as determined by the degree of repeatability of the image controls. Level 1 is too sensitive to noise, and levels 4 and 5 are too insensitive to changes.

Without any image enhancement or with the use of conventional image enhancement such as contrast stretching and histogram equalization, the correlation scores between images with and without the absorption artifact were well above 0.90, effectively preventing useful comparison between images.

The sources cited above are incorporated by reference, herein. While the present invention has been described with reference to the presently preferred embodiments, it will be apparent to those skilled in the art that various changes and modifications may be made without departing from the spirit and scope of the invention, as defined by the claims below. The following computer program is subject to copyright protection. ©1998 Electro-Optical Sciences, Inc.

What is claimed is:

1. A system for acquiring images of a tooth, comprising:
   an illumination source;
   an electronic camera; and
   a mouthpiece for being coupled to the illumination source and the electronic camera, the mouthpiece having an output portion to transfer light from the illumination source to the tooth and an input portion to receive light passing through the tooth, the mouthpiece being anchorable in the mouth with respect to a tooth to provide a position reference and an angle reference for light radiation relative to at least one surface of the tooth and an angle reference for the line of sight during imaging relative to at least one surface of the tooth, the mouthpiece being anchorable in a repeatable manner to provide the same position and angle reference.

2. The system of claim 1, further comprising at least one optical fiber coupled to the illumination source, for conveying light from the illumination source through at least a portion of the mouthpiece to the output portion.

3. The system of claim 1, further comprising:
   computer for being coupled to the electronic camera.

4. The system of claim 3, wherein the computer automatically changes the intensity of the light to avoid saturation of an image recorded by the camera.

5. The system of claim 3, wherein the computer comprises means for digitally representing the image of the tooth through wavelet transformation.

6. The system of claim 5, wherein the computer comprises means for segmenting the tooth in the digital image through chaining local maxima in wavelet amplitude.

7. The system of claim 3, wherein the computer comprises means for comparing a current image of a tooth to an image of the same tooth prepared at an earlier time, at substantially the sane position and angle references as the current image, to obtain an image of the substantially same portion of the tooth as the current image, to identify changes in the tooth over time.

8. The system of claim 7, wherein the means for comparing comprises means for analyzing the numerical correlation between the current image and the previously taken image.

9. The system of claim 8, wherein the means for analyzing comprises means for correlating segmented images of the tooth in the wavelet domain.

10. The system of claim 8, wherein the means for analyzing comprises means for correlating segmented images of the tooth in the spatial domain.

11. The system of claim 3, wherein the computer comprises means for automatically adjusting the range of intensity of the digital image to avoid overexposure and underexposure of the digital image.

12. The system of claim 1, further comprising means for changing the wavelength of the output of the illumination source to obtain images at different wavelengths for the identification of tooth conditions by comparison of the images obtained at different wavelengths.

13. The system of claim 1, wherein the camera is part of the mouthpiece.

14. The system of claim 13, wherein the mouthpiece further comprises a mirror proximate the input portion and at least one lens, the mirror for reflecting light passing through the tooth and input portion to the lens, which focuses the light onto the camera.

15. The system of claim 14, further comprising a second mirror proximate the output portion and an optical fiber for transferring light from the illumination source to the second mirror for reflection out of the output portion onto the tooth, the second mirror being rotationally coupled to the mouthpiece to illuminate the tooth at different angles.

16. The system of claim 1, further comprising means for digitizing the image.

17. The system of claim 16, wherein the means for digitizing is a charge-coupled-device image array which is part of the electronic camera.

18. The system of claim 1, wherein the mouthpiece comprises a prong extending from its distal end for bearing against a proximal surface of the tooth and a plate at its distal end for bearing against the occlusal or incisal surface of the tooth.

19. The system of claim 18, wherein the mouthpiece further comprises a portion for bearing against a lingual or buccal surface of the tooth.

20. The system of claim 1, wherein the input portion and the output portion of the mouthpiece define a space therebetween to receive the tooth.

21. The system of claim 20, wherein the mouthpiece comprises a base with a distal end and a separable portion including an input portion and an output portion for being connected to the base.

22. The system of claim 3, further comprising:
a monitor for being coupled to the digital processing unit to display images of the tooth.

23. An apparatus for illuminating a tooth of interest comprising:

a handle having a front end;

a horizontal plate for resting on an occlusal or incisal surface of the tooth, the plate being coupled to the front end, and having a first edge proximate the front end and a second edge distanced from the front end;

a vertical wall depending from the second edge, perpendicular to the horizontal plate;

a first prong extending from an edge of the vertical wall towards the front end, for bearing against a proximal surface of the tooth;

means for illuminating the tooth, located in the vertical wall adjacent the first prong; and means for receiving the light passing through the tooth, the means for receiving depending from the front end, opposite the illuminating means and distanced from the illuminating means a sufficient distance for the tooth to be received therebetween.

24. The apparatus of claim 23, wherein the illuminating means comprises an optical fiber and a first mirror adjacent an output of the optical fiber for reflecting light emitted from the optical fiber through the tooth; and the receiving means comprises a second mirror and a third mirror, wherein the second mirror reflects light passing through the tooth to the third mirror, which reflects the light through the handle.

25. The apparatus of claim 24, wherein the receiving means further comprises at least one lens and a charge-coupled-device, wherein the at least one lens focuses light reflected from the third mirror onto the charge-coupled-device.

26. The apparatus of claim 24, wherein the receiving means further comprises at least one lens and at least one optical fiber, wherein the at least one lens focuses light reflected from the third mirror into the at least one optical fiber.

27. The apparatus of claim 23, further comprising a second prong extending from the vertical wall, wherein the first and second prongs are on opposite sides of the illuminating means.

28. The apparatus of claim 23, wherein the horizontal plate is rotatably coupled to the front end such that rotation of the handle with respect to the tooth enables the receiving means to receive light passing through the tooth at different angles.

29. The apparatus of claim 23, wherein the handle and the front end are separable.

30. The apparatus of claim 29, further comprising two separable front ends for use depending on the location of the tooth, the separable front ends being mirror images of each other.

31. An apparatus for use in transillumination imaging of a tooth of interest in a mouth, comprising:

a base with a front end;

a first portion for resting on an occlusal or incisal surface of the tooth, extending from the front end;

a second, vertical portion extending from the first portion with a prong extending perpendicular to the second, vertical portion, for bearing against a proximal surface of the tooth to prevent lateral movement of the apparatus during imaging;

means for illuminating the tooth coupled to the front end; and means for receiving light passing through the tooth to form an image of the transilluminated tooth, said means being coupled to the front end, wherein the illuminating means and the receiving means define a region for receiving at least a portion of the tooth therebetween;

the first portion and the prong for engaging the tooth in the mouth in a repeatable manner to define a position reference and angle reference for light radiation relative to at least one surface of the tooth, and an angle reference for the line of sight during imaging relative to at least one surface of the tooth.

32. The apparatus of claim 31, wherein the receiving means is coupled to the front end, opposite to the illuminating means.

33. The apparatus of claim 31, further comprising a second vertical portion extending from the horizontal portion, adjacent to the first vertical portion, for bearing against a lingual or buccal surface of the tooth.

34. A system for acquiring images of a tooth, comprising:

an illumination source;

an electronic camera;

a mouthpiece for being coupled to the illumination source and the electronic camera, the mouthpiece having a frame including a base frame portion for being engaged by an operator and an extended frame portion extending from the base portion, the extended frame portion having an output portion for transferring light radiation to the tooth and an input portion for receiving light radiation passing through the tooth, the extended frame portion of the mouthpiece being anchorable to the tooth by engaging the tooth in a repeatable position with respect to the tooth to define a position reference and angle reference for light radiation relative to at least one surface of the tooth, and an angle reference for the line of sight during imaging relative to at least one surface of the tooth, the extended frame portion being rotatable with respect to the base;

a processing unit for being coupled to the electronic camera; and a monitor for being coupled to the digital processing unit, to display images of the tooth.

35. A dental mouthpiece for use in transillumination imaging of a tooth of interest in a mouth, comprising:

a handle portion;

a front portion extending from the handle portion, the front portion having a distal end with a surface for bearing against an occlusal or incisal surface of a tooth and an extending portion depending from the surface, the extending portion having a parallel portion extending parallel to the horizontal surface for engaging a proximal surface of the tooth;

an output portion for conveying light radiation from the front portion towards the tooth; and an input portion for receiving light radiation passing through the tooth;

the front portion and parallel portion for engaging the tooth in the mouth in a repeatable manner to define a position reference and an angle reference for light radiation relative to at least one surface of the tooth, and an angle reference for the line of sight during imaging relative to at least one surface of the tooth.

36. The dental mouthpiece of claim 35, further comprising a second parallel portion depending from the horizontal surface and extending parallel thereto, for bearing against the lingual or buccal surface of the tooth, the second parallel portion being adjacent to the first parallel portion.

37. A method of acquiring images of a tooth comprising:

anchoring a mouthpiece in a position in a mouth with respect to the tooth in a repeatable manner;

illuminating a surface of the tooth with light radiation provided through the mouthpiece;

receiving light radiation passing through the tooth by the mouthpiece; and electronically imaging the tooth from the light received by the mouthpiece;

wherein the anchoring step comprises providing a position reference and an angle reference for the light radiation relative to at least one surface of the tooth and an angle reference for the line of sight during imaging relative to at least one surface of the tooth, the mouthpiece being anchorable in a repeatable manner to provide the same position and angle references.

38. The method of claim 37, wherein at least one of the reference positions is defined in the plane tangent to the illuminated tooth surface.

39. The method of claim 37, further comprising first selecting at least one surface of the tooth as a reference, wherein the illuminating step comprises illuminating a surface of the tooth at a lateral position defined with respect to a reference surface and the imaging step comprises imaging the tooth at an axial position and angle through the tooth defined with respect to a reference surface.

40. The method of claim 37, further comprising controlling the angle of illumination of the surface of the tooth.

41. The method of claim 37, further comprising controlling the relative angle of illumination and line of sight with respect to the tooth.

42. The method of claim 37, further comprising:

providing a mouthpiece with a distal end and a rotatable portion at the distal end, wherein the light radiation for illuminating the tooth is provided from one of the distal end of the mouthpiece and the rotatable portion and light radiation is received after passing through the tooth by the other of the distal end of the mouthpiece and the rotatable portion; and adjusting the relative angle of illumination and line of sight by rotation of one of the mouthpiece and the rotatable portion.

43. The method of claim 37, further comprising providing a mouthpiece with a rotatable portion and coupling the light radiation to an electronic camera for imaging the tooth through the rotatable portion of the mouthpiece.

44. The method of claim 37, wherein the anchoring step comprises positioning the mouthpiece against contact points in between the tooth of interest and an adjacent tooth.

45. The method of claim 37, wherein the anchoring step comprises positioning a portion of the mouthpiece against a proximal surface of the tooth.

46. The method of claim 45 further comprising positioning a portion of the mouthpiece against an incisal or occlusal surface of the tooth.

47. The method of claim 46, further comprising positioning a portion of the mouthpiece against a lingual or buccal surface of the tooth.

48. The method of claim 37, wherein the electronic imaging step comprises imaging the tooth from a non-illuminated surface of the tooth.

49. The method of claim 48, further comprising replacing a first separable portion of the mouthpiece with a second separable portion of the mouthpiece depending on the location of the tooth, wherein the first and second separable portions are mirror images of each other.

50. The method of claim 37, further comprising replacing a first separable portion of the mouthpiece with a second separable portion of the dental mouthpiece.

51. The method of claim 37, further comprising providing a mouthpiece having a base portion connected to an illumination source.

52. The method of claim 51, further comprising providing a mouthpiece with a miniature electronic camera having a digital output.

53. The method of claim 51, further comprising providing fiber optics to transfer illumination from the illumination source through the base portion of the mouthpiece.

54. The method of claim 37, comprising digitally imaging the tooth.

55. The method of claim 54, further comprising adjusting the range of intensity of the digital image to avoid overexposure and underexposure.

56. The method of claim 54, further comprising sequentially repeating the illuminating step and the imaging step and automatically adjusting the intensity of light reaching the electronic camera under software control to avoid saturation of the image recorded by the camera.

57. The method of claim 53, further comprising digitally imaging the tooth and segmenting the tooth in the image through chaining local maxima in wavelet amplitude.

58. The method of claim 37, further comprising comparing at least a portion of a current image of the tooth to an image including substantially the same portion of the tooth previously obtained at substantially the same position reference and angle references to identify changes in the tooth over time.

59. The method of claim 58, further comprising analyzing the numerical correlation between the current image and the previously obtained image.

60. The method of claim 59, comprising correlating segmented images of a region of interest of the tooth in the wavelet domain.

61. The method of claim 59, comprising correlating segmented images of the tooth in the spatial domain.

62. The method of claim 37, wherein the illuminating step comprises illuminating the tooth at a plurality of wavelengths and the imaging step comprises imaging the tooth at the plurality wavelengths, for diagnostic purposes.

63. A method for monitoring changes with time in a region of interest of a tooth comprising:
    anchoring a mouthpiece to the tooth at a first point in time to define a reference position with respect to coordinate axes of at least two dimensions;
    illuminating a surface of the tooth with light radiation provided through the mouthpiece at a first angle defined with respect to the reference position and coordinate axes;
    digitally imaging the tooth by light passing through the tooth and received by the mouthpiece at a second angle defined with respect to the reference position and coordinate axis to create at least one digital image of at least a portion of the tooth that includes a region of interest;
    anchoring a dental mouthpiece to the same tooth in the mouth of the same patient at a later point in time to define substantially the same reference position with respect to the same coordinate axis as at the first point in time;
    illuminating substantially the same surface of the tooth with light radiation provided through the mouthpiece at substantially the first angle defined with respect to the reference position and coordinate axes;
    digitally imaging the tooth by light passing through the tooth and received by the mouthpiece at substantially the second angle defined with respect to the reference position and coordinate axes to create at least one, second digital image of the tooth including at least substantially the same region of interest of the tooth as the first image; and
    comparing the first and second digital images to identify changes in the region of interest of the tooth.

64. The method of claim 63, further comprising imaging the tooth from a non-illuminated surface of the tooth of interest.

65. A method of acquiring images of a tooth of interest in a mouth, comprising:
    anchoring a mouthpiece in a position with respect to at least two coordinate axes defined with respect to a tooth of interest in the mouth by engaging at least a proximal surface of the tooth of interest to anchor the mouthpiece with respect to a lateral axis of the tooth of interest to define a position reference and an angle reference for light radiation relative to at least one surface of the tooth, and an angle reference for the line of sight during imaging relative to at least one surface of the tooth;
    illuminating a surface of the tooth with light radiation provided through the mouthpiece;
    receiving light passing through the tooth of interest by the mouthpiece; and
    electronically imaging the tooth of interest.

66. The method of claim 65, further comprising positioning a portion of the mouthpiece against an incisal or occusal surface of the tooth to further anchor the mouthpiece with respect to a vertical axis.

67. The method of claim 66, further comprising positioning a portion of the mouthpiece against a lingual or buccal surface of the tooth to further anchor the mouthpiece with respect to an axial axis through the tooth.

68. The method of claim 67, wherein the anchoring step comprises positioning the mouthpiece against contact points in between the tooth and an adjacent tooth to further anchor the dental mouthpiece with respect to a lateral axis with respect to the tooth.

69. A method of acquiring images of a tooth with a dental mouthpiece, the mouthpiece having a frame including base frame portion and a rotatable frame portion coupled to the base portion, comprising;
    anchoring the dental mouthpiece in position with respect to a tooth in a repeatable manner to define a position reference and an angle reference for light radiation relative to at least one surface of the tooth, and an angle reference for the line of sight during imaging relative to at least one surface of the tooth;
    illuminating a surface of a tooth with light radiation provided through the mouthpiece, the light exiting the mouthpiece through the rotatable frame portion;
    coupling the light radiation passing through the tooth of interest to an electronic camera via the rotatable frame portion of the mouthpiece; and
    electronically imaging the tooth of interest with the electronic camera.

* * * * *